United States Patent [19]

Fujiwara et al.

[11] Patent Number: 5,498,550

[45] Date of Patent: Mar. 12, 1996

[54] DEVICE FOR COLLECTING OR PREPARING SPECIMENS USING MAGNETIC MICRO-PARTICLES

[75] Inventors: Koichi Fujiwara, Mito; Hiromichi Mizutani, deceased, late of Tokyo, Japan, by Hiroko Mizutani, legal representative

[73] Assignee: Nippon Telegraph & Telephone Corporation, Tokyo, Japan

[21] Appl. No.: 249,152

[22] Filed: May 25, 1994

Related U.S. Application Data

[62] Division of Ser. No. 991,507, Dec. 17, 1992, Pat. No. 5,340,749, which is a continuation of Ser. No. 344,239, Apr. 26, 1989, abandoned.

[30] Foreign Application Priority Data

| Apr. 26, 1988 | [JP] | Japan | 63-102919 |
| Jun. 24, 1988 | [JP] | Japan | 63-156519 |
| Oct. 28, 1988 | [JP] | Japan | 63-272106 |
| Dec. 5, 1988 | [JP] | Japan | 63-307579 |
| Mar. 27, 1989 | [JP] | Japan | 1-74245 |

[51] Int. Cl.$^6$ .............................. G01N 33/553
[52] U.S. Cl. .............. 436/526; 435/5; 435/7.1; 435/30; 435/34; 435/174; 435/243; 435/261; 435/287.2; 435/803; 435/971; 435/283.1; 436/806; 436/824; 210/695; 210/222; 250/311; 250/442.11; 356/38
[58] Field of Search .................. 422/101, 104; 435/5, 7.1, 7.21, 7.23, 7.24, 30, 34, 173, 174, 243, 261, 287, 292, 803, 961, 971, 173.1; 436/63, 64, 177, 178, 526, 805, 806, 824; 210/695, 222; 250/311, 440.11, 442.11; 356/36, 38, 39, 244

[56] References Cited

U.S. PATENT DOCUMENTS

| 3,970,518 | 4/1976 | Giaever | 436/526 X |
| 4,157,323 | 6/1977 | Yen et al. | 422/68 X |
| 4,375,407 | 3/1983 | Kronick | 436/526 X |

(List continued on next page.)

FOREIGN PATENT DOCUMENTS

0206077 12/1986 European Pat. Off. .

(List continued on next page.)

OTHER PUBLICATIONS

35th General Meeting of Japan Virus Association, Lecture No. 4011, p. No. 299, 1987.
Mizutani et al, "Detection of EB Virus Infected Cells by Magnetic Immunoassay", Lecture M–26, Rapid Viral Diagnosis, International Symposium in Helsinki University, Jun. 20, 1989.
Fujiwara et al, "A New Method for Detection of Viral Antigens", Lecture M–31, International Symposium in Helsinki University, Jun. 20, 1989.
Chemical Abstracts, vol. 108, 1988, p. 663, abstract No. 160091g, Columbus, Ohio, US; M. Seki et al, "Observations of ultrafine zinc ferrite (ZnFe2C4) particles with transmission electron microscopy", J. Appl. Phys., 1988, 63(5), 1424–1427.

*Primary Examiner*—Carol A. Spiegel
*Assistant Examiner*—Susan C. Wolski
*Attorney, Agent, or Firm*—Frishauf, Holtz, Goodman, Langer & Chick

[57] ABSTRACT

A device for collecting a specimen, including (a) a test vessel for containing a solution containing an immunocomplex, which is a complex as a result of an antigen-antibody reaction between a specimen and a magnetic-labeled antibody containing a magnetic micro-particle and an antibody fixed to the micro-particle, (b) an external magnetic field generating device for generating a magnetic field, preferably a gradient magnetic field and applying it to the solution in the test vessel to effect local concentration of the immunocomplex to a predetermined position, (c) a magnetic member for collecting the immunocomplex at the position of local concentration, and (d) a moving mechanism for achieving relative movement between the magnetic member and the test vessel.

7 Claims, 12 Drawing Sheets

U.S. PATENT DOCUMENTS

| | | | |
|---|---|---|---|
| 4,628,037 | 12/1986 | Chagnon et al. | 436/526 |
| 4,710,472 | 12/1987 | Saur et al. | 435/287 |
| 4,729,949 | 3/1988 | Weinreb et al. | 435/30 |
| 4,738,773 | 4/1988 | Muller-Ruchholtz et al. | 209/214 |
| 5,252,493 | 10/1993 | Fujiwara et al. | 436/526 |

FOREIGN PATENT DOCUMENTS

| | | |
|---|---|---|
| 0287665 | 10/1988 | European Pat. Off. . |
| 61-293562 | 12/1986 | Japan . |
| 63-79070 | 4/1988 | Japan . |
| 63-108265 | 5/1988 | Japan . |
| 63-106559 | 5/1988 | Japan . |
| 63-188764 | 8/1988 | Japan . |
| 63-188766 | 8/1988 | Japan . |
| 63-315952 | 12/1988 | Japan . |
| 63-315951 | 12/1988 | Japan . |
| 64-29768 | 1/1989 | Japan . |
| 1-107151 | 4/1989 | Japan . |
| 1-109263 | 4/1989 | Japan . |
| WO/88/02118 | 9/1987 | WIPO . |

100nm

100nm

DEVICE FOR COLLECTING OR PREPARING SPECIMENS USING MAGNETIC MICRO-PARTICLES

This is a division of application Ser. No. 07/991,507 filed Dec. 17, 1992, now U.S. Pat. No. 5,340,749 issued Aug. 23, 1994, which is a continuation of application Ser. No. 07/344,239 filed Apr. 26, 1989 (abandoned).

BACKGROUND OF THE INVENTION

1. Field of the Invention

The present invention relates to magnetic micro-particles, a method and an apparatus for collecting specimens using an antigen-antibody reaction, a method and a device for preparing specimens, which are suitable for use in immunonological diagnosis, biotechnology such as cell engineering, as well as virology and immunology.

2. Prior Art

Development of immunoassay methods utilizing an antigen-antibody reaction is now being made on a global scale as an early detection method for new virus-based diseases such as acquired immune deficiency syndromes (AIDS) and adult T-cell leukemia as well as various cancers. Tests now practiced are antibody tests designed to detect antibodies produced by an immune reaction in humans after infection with immunogens and therefore they are disadvantageous in that even when infection occurred, presence of an infection is not judged during the latent period before an antibody is produced. For this reason, there is a keen demand for developing a test method which permits direct detection of viruses and allows early diagnosis.

As for the direct detection method for detecting viruses, a blood agglutination method has been known. This method, however, is poor in detection sensitivity, and it was necessary to cultivate and multiply viruses to a population of at least 10,000,000 individuals/ml, which operation is troublesome and time consuming. Furthermore, it was necessary in this method to find sensitive host cells suitable for cultivating viruses since host cells are different for different viruses. In addition, a search or screening of sensitive cells was difficult since cultivation of viruses infectious to humans using animal cells involves a technological bottleneck.

In the case of viral hepatitis, for example, there occurs very often accidents that medical workers are infected with virus from patients since the disease is notoriously infectious, causing a social problem. As for vital hepatitis, type A hepatitis virus and type B hepatitis virus are known as pathogens and vaccines have been prepared. However, no pathogenic virus has been found yet for non-A and non-B vital hepatitis despite the fact that the presence of such virus was supposed well before, and therefore, no accurate therapy has been established yet.

Morphological observation of virus for confirming its presence is achieved only by electron microscopic observation. The morphological observation makes it possible to judge which group the virus in question belongs to, and when a new virus is found, it is indispensable to finally confirm the virus under an electron miloscope. In this ease, however, it is difficult to make observation unless rims is present in a high concentration since virus is in the order of 20 to 200 nm in size and since a narrow region in the order of μm is to be observed. Accordingly, it has heretofore been practically impossible to detect such a minute amount of virus that only about 10 individuals/ml are present in a solution. The same is true for diagnosis in the level of cells such as cancer cells.

In the case of cancers, initially only a single cell is cancerated and in a long period time the subject falls ill. Diagnosis therefor presently employed involving use of an endoscope, CT scanner, pathological tests, and the like is carried out mostly with the eyes of a doctor or physician, resulting in that at the moment when a subject was diagnosed to suffer cancer, that which is difficult to diagnose with one's eyes has already completed metabasis or metastasis, and a physical operation does seldom prevent palindromia. If diagnosis can be performed before palindromia takes place at a level of a cell, palindromia can be avoided and it will be possible to cure cancers by immunological therapy without operations. With view to this, immunological diagnosis for cancers such as one using a tumor marker is now under research and development although little is put in practice an early diagnosis method.

Biotechnology such as genetic engineering, cell engineering or a like has paid attention as an approach for finding a breakthrough to the difficult situation encountered in the medical field and bringing a technological innovation thereto. There is a possibility that with the use of biotechnological techniques put in practice, e.g., cell level immunological diagnosis techniques utilizing an antigen-antibody reaction, and gene level immunological diagnosis technique utilizing hybridization of DNA (formation of double strands) that early diagnosis of various diseases can be performed. For this reason, development of early diagnosis techniques is promoted on a global scale.

Upon carrying out research at a level of a virus, cancer cell or gene freely utilizing such biotechnological techniques, techniques are indispensable which enable detection and collection of specimens such as viruses, cancer cells, etc. which are the subject of the research.

In order to detect specimens with a high detection sensitivity, the present inventors previously studied laser magnetic immunoassay methods as described in WO/88/02118 (PCT/JP87/00694 corresponding to Japanese Patent Application Nos. 61-224567, (51-252427, (51-254164, (52-22062, (52-22063, 62-152791, 62-152792, and 62-184902), Japanese Patent, Application (Kokai) No. 1-107151 corresponding to Japanese Patent Application No. 62-264319, and Japanese Patent Application No. 62-267481. The methods are characterized by using a laser beam in detecting the presence of absence of an antigen-antibody reaction, using magnetic micro-particles as a labeling material and radiating a laser beam to a concentrated specimen and detecting reflected light or a like outgoing light from the specimen, and they permit ultramicro detection of specimens in the order of picograms. Particularly, the technology described in Japanese Patent Application No. 62-184902 applies a magnetic field to a solution containing a magnetic-labeled specimen to guide and concentrate the specimen to a laser beam radiation area on the surface of the solution using a magnet The guidance with a magnet causes minute protrusion on the surface of the solution and interference fringes generated in reflected light, the occurrence of which depends on the degree or height of the protrusion, are detected. This gives detection of the specimen. This method permits de:cotton of virus in a population in the order of 10 individuals/ml in contract to the conventional EIA in which detection is only possible when virus is present in a population in the order of 10,000,000 individuals/ml.

Based on the above-described assay method, the present inventors have labeled antigens or antibodies with magnetic micro-particles and carried out direct detection of viruses for the first time. It is now being confirmed that the laser magnetic immunoassay method has a detection sensitivity higher than RIA referred to hereinbelow which has been said to be most sensitive. For example, when performing virus detection experiments using inactivated type A and type B influenza viruses as a model for virus, detection of viruses in a population in the order of one individual/ml was successful as the present inventors reported in 35th General Meeting of Japan Virus Association (November of 1987, Lecture No. 4011, "Virus detection experiment using a newly developed immunoassay apparatus").

However, techniques for efficiently collecting specimens such as virus, cancer cells or lymphocytes have remained on the way of development and have not been put in practice yet.

On the other hand, examples of conventional micro-immunoassay methods that have been put in practice include radioimmunoassay (RIA), enzyme-immunoassay (EIA), fluorescence-immunoassay (HA), etc. These methods use antigens or antibodies which are labeled with an isotope, an enzyme or a fluorescent substance in order to detect the presence or absence of corresponding antibodies or antigens, respectively, that react specifically therewith.

RIA is a method in which the radioactivity of an isotope used as a label is measured to quantitatively determined the amount of the specimen which has contributed to the antigen-antibody reaction, and at present it is only RIA that permits ultramicro measurement at a detection sensitivity in the order of picograms. However, it has many restrictions in its practice because it uses radioactive substances as a label substance and needs special installment and because decrease of effect of labeling due to half-life and other factors must be taken into consideration. Furthermore, considering the present social environment in which disposal of radioactive wastes is a big social problem, practice of RIA is naturally restricted.

On the other hand, methods using enzymes or fluorescent substances as a label are methods in which the amount of the specimen which has contributed to the antigen-antibody reaction is measured by determining coloring or luminescence, and therefore do not have restrictions that are imposed on RIA. However, the detection limit of these methods is in the order of nanograms.

As described above, among the conventional immunoassay methods, RIA, which has a high detection sensitivity, has many restrictions in practicing it due to use of radioactive substances, and on the other hand, EIA, FIA and the like methods, which are easy to practice, have a low detection sensitivity and they are applied mainly to tests for antibodies. Since tests for antibodies are designed to detect antibodies formed by immune reactions in humus, it is impossible in principle to directly detect viruses in blood.

In the labeling methods such as RIA, EIA and FIA described above, they are performed by adding to a specimen an excess amount of a labeling reagent such as a radioactive isotope, an enzymes or a fluorescent dye, respectively, and allowing an antigenantibody reaction between the specimen and the labeling reagent to occur, followed by removing unreacted labeling reagent by washing. Therefore, the more the amount of the specimen decreases the more excess the amount of the labeling reagent than the specimen, which causes a serious problem that the labeling reagent that remained unremoved after washing cause non-specific reactions.

Furthermore, application of laser magnetic immunoassay to electron microscopic observation of viruses, cancer cells, lymphocyte and the like specimens needs improvement in technology for the preparation of specimens in high efficiency.

Based on the results of detection for viruses using the laser magnetic immunoassay, the present inventors have presented lectures entitled "Detection of EB virus infected cells by magnetic Immunoassay", Lecture No. M-26, and "A new method for detection of virus antigens", Lecture No. M-31, in an international symposium on basis of chemotherapy of viruses and its clinical application held on Jun. 20, 1989 at Helsinki University in Finland.

The present inventors proposed to name the new method "MIA (magnet immunoassay) method". In order to take advantage of MIA method, it is important to develop a method for preparing specimens in which a very small amount of a specimen can surely be labeled magnetically.

Wolfgang Mueller Ruffoltz et al., Japanese Paint Application (Kokai) No. 61-293562, "Separator for magnetically removing magnetizable particles", disclose a separator using an electromagnet. The separator, which is designed to fractionate biological materials with resort to magnetic microspheres to remove cells, antigens, antibodies, enzymes, etc., is constructed such that Teflon piping called a separation unit: and having a length of 1 to 200 cm and a diameter 0.1 to 6 mm is wound so as to form a circle is fitted in an electromagnet, and is unsuitable if applied to preparation of specimens to be measured by the laser magnetic immunoassay method because a very large amount of magnetic-labeled antibody is to be used, thus failing to efficiently recovering specimens bound to the magnetic-labeled antibody.

A further problem of the separator is that if the length of the Teflon piping was reduced most of the specimen would pass through the piping without reacting with the magnetic-labeled antibody since the magnetic-labeled antibody is held only on the wall of the Teflon piping although the amount of the magnetic-labeled antibody to be used would be reduced.

A disadvantage common to the conventional met:hods is the fact that the smaller the size of ultramicro-particles of a magnetic substance the more difficult it is to surely hold the magnetic-labeled antibody in an electromagnet. That is, when ultramicro specimen such as a virus is labeled magnetically, it is preferred that the magnetic-labeled antibody is smaller than the virus. However it is known that the magnetic micro-particles composed of a ferromagnetic substance become non-ferromagnetic and converted to a superparamagnetic substance which does not respond to a magnet when their particle size becomes smaller. For example, magnetite is converted to superparamagnetic when the particle size is not larger than 10 nm, and when magnetic-labeled antibody is prepared using magnetite with a particle size of not larger than about 10 nm, it takes an hour or more according to the conventional methods to gather the magnetic-labeled antibody using a magnet.

Therefore, further improvement is desired.

SUMMARY OF THE INVENTION

Therefore, the present invention provides a method and device for collecting a specimen and those for preparing a specimen characterized by magnetically labeling a specimen with a magnetic-labeled body composed of a micro-particle of a magnetic substance and an antibody or antigen bound thereto, and applying a gradient magnetic field to the magnetic-labeled specimen to locally concentrate the labeled specimen to a predetermined position and recovering an immunocomplex efficiently.

In a preferred embodiment, the present invention enables acceleration of the antigen-antibody reaction by means of a magnetic force to efficiently perform magnetic labeling of the specimen.

Hereinafter, the present invention will be described in detail with reference to embodiments which are directed to improvements relating to collection of specimens, preparation of specimens for electron microscopic observation, and preparation of specimens for use in laser magnetic immunoassay methods previously proposed by the present inventors.

DETAILED DESCRIPTION OF THE INVENTION

Figure 1:
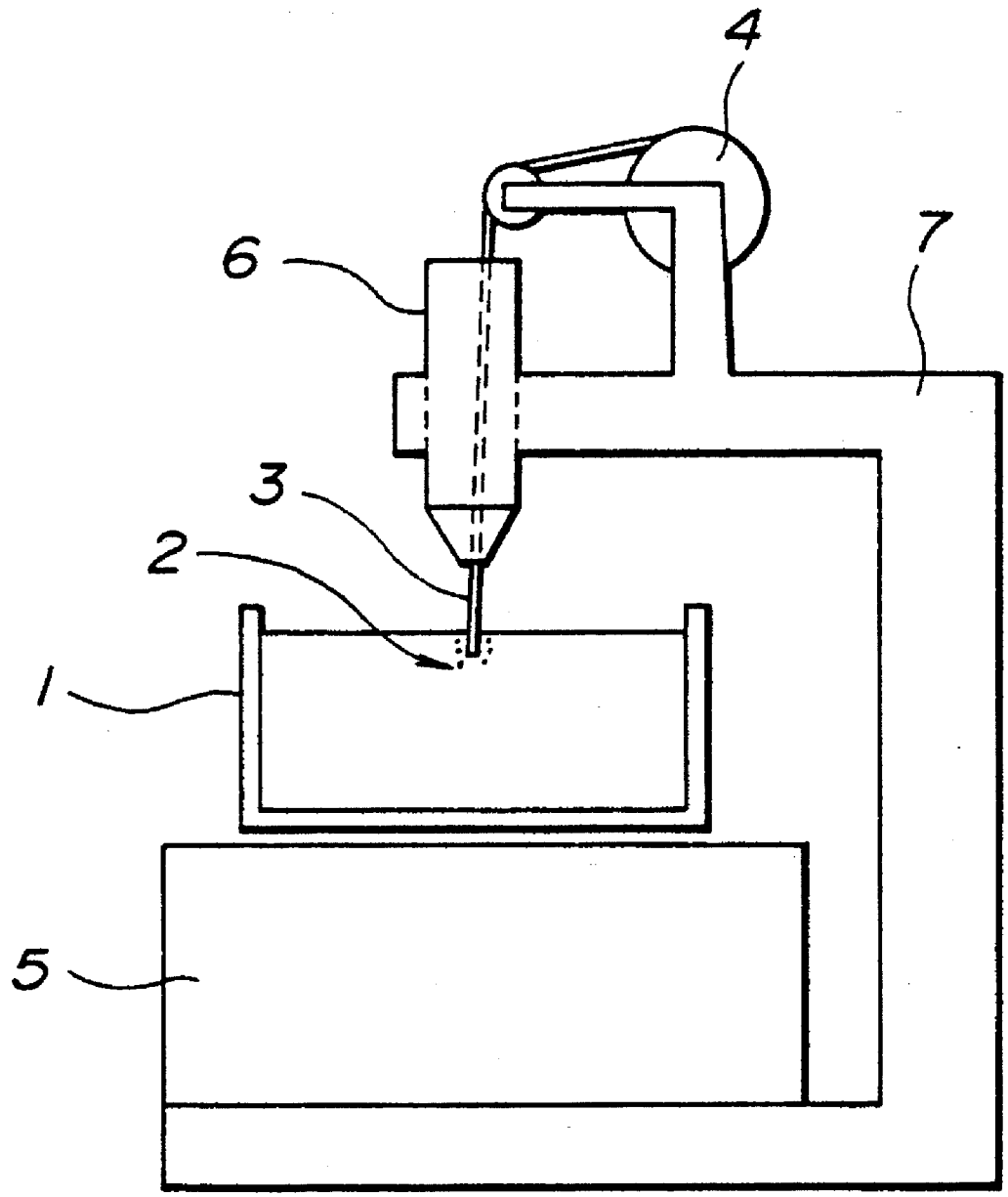
FIG. 1 is a schematic illustration of a specimen collecting device according to one embodiment of the present invention.

According to a first embodiment of the present invention, there is provided a method for collecting a specimen, comprising a first step of subjecting a specimen and a magnetic-labeled antibody composed of a magnetic micro-particle and an antibody fixed to the micro-particle to an antigen-antibody reaction to form an immunocomplex which is a complex of the specimen and the magnetic micro-particle, a second step of performing local concentration of the immunocomplex to a predetermined position by applying an external magnetic field, preferably a gradient magnetic field, and a third step of collecting the immunocomplex at the position of local concentration.

According to a second embodiment of the present invention, there is provided a method for collecting a specimen, in which the specimen in the first step of the first embodiment above is fixed to a non-magnetic particle having a mass greater than the magnetic-labeled antibody prior to subjecting the specimen and the magnetic-labeled antibody to an antigen-antibody reaction, and unreacted magnetic-labeled antibody is separated and removed by centrifugation.

In these methods, specimens such as virus, cancer cells and lymphocytes can be collected. In the method according to the second embodiment, the specimen can be fixed to the non-magnetic particles, for example, by activating the surface of the non-magnetic particle by a known method and allowing the specimen to adsorb non-specifically on the activated surface, or by fixing a known antibody onto the surface of the non-magnetic particle and subjecting the specimen and the known antibody to an antigen-antibody reaction. In addition, in these methods, it is preferred to insert a magnetic member or piece at the position of local concentration to attract thereon the immunocomplex followed by withdrawing the magnetic member, in order to efficiently collect the immunocomplex concentrated at the position of local concentration.

According to a third embodiment of the present invention, there is provided a device for collecting a specimen, comprising a test vessel for containing a solution containing an immunocomplex, which is a complex formed as the result of antigen-antibody reaction between a specimen and a magnetic-labeled antibody composed of a magnetic micro-particle and an antibody fixed to the micro-particle, an external magnetic field generating device for generating a magnetic field, preferably a gradient magnetic field and applying it to the solution in the test vessel to effect local concentration of the immunocomplex to a predetermined position, a magnetic member for collecting the immunocomplex at the position of local concentration, and a moving mechanism for achieving relative movement between the magnetic member and the test vessel.

In the device for collecting a specimen according to the present invention, the test vessel is preferably a vessel which has an upward opening in order to perform the local concentration and collection of the immunocomplex efficiently. The gradient magnetic field generating-device may desirably comprise a magnet arranged below the test vessel and a pole piece placed just above the surface of the liquid contained in the vessel and opposing the magnet.

According to the present invention, the specimen can surely be trapped or collected by external magnetic force since it is bound to the magnetic-labeled antibody by an antigen-antibody reaction. When a gradient magnetic field is designed such that the magnetic potential of the position of collection is the highest is applied to the magnetic-labeled antibody as an external magnetic force, the magnetic-labeled antibody is localized and concentrated to the position of collection, and the objective specimen bound to the magnetic-labeled antibody can be collected by inserting the collecting device to the position of concentration to collect the magnetic-labeled antibody. In this case, the specimen is collected together with unreacted magnetic-labeled antibody.

When it is intended to collect only the specimen, a method can be used in which a non-magnetic particle having a mass sufficiently greater than the magnetic-labeled antibody. That is, after the specimen is fixed to the non-magnetic particle, the magnetic-labeled antibody is bound thereto and then the reaction mixture is centrifuged to precipitate only the immunocomplex, thus enabling the separation and removal of unreacted magnetic-labeled antibody. In addition: activation of the surface of the non-magnetic particle to non-specifically bind the specimen is effective for finding unknown virus and the like or for the collection of a very small amount of specimen. On the other hand, it is suitable for collecting only the specimen to specifically bind the specimen with an antibody-coated non-magnetic particle.

The device for collecting a specimen according to the present invention is suitable for practicing the above-described methods by use of the upwardly opening test vessel, the gradient magnetic field generating device comprising the magnet and the pole piece enables selection of any desired point on the surface of the liquid contained in the test vessel as a position of local concentration at which the highest magnetic field is applied, thus permitting collection of the immunocomplex guided and concentrated to the position of local concentration using the magnetized magnetic member by magnetically attracting on the surface thereof.

Taking advantage of the above feature of the present invention, it is possible to guide and concentrate a specimen to a position of electron microscopic observation selected on the device for collecting a specimen so that an unknown virus that is difficult to cultivate can be detected directly even in a very small amount, which greatly adds to the development of virology. For example, the present invention contributes to finding non-A or non-B type hepatitis virus. It also useful for early diagnosis of cancer cells and the like on cellular level, and can collect a very small amount of cancer cells which are leaving the cancerous tissue and metastasizing into body fluid such as blood. Moreover, it is also possible according to the present invention to collect physiologically active substances such as enzymes and hormones occurring but in a minute amount which bind specifically by antigen-antibody reaction.

The method of the present invention is applicable not only to electron microscopic observation of specimens, but also to extraction of only specimens by adjusting the pH value of the liquid to 3.0 to 3.5 after the collection of the desired specimen to release the magnetic-labeled antibody from the specimen and removing the magnetic-labeled antibody by means of a magnet. The extracted specimen can be utilized as a material for use in biochemical analysis, genetic analysis and genetic recombination.

As stated above, the present invention is very useful in the medical and therapeutical fields, scientific fields such as molecular biology, biotechnological fields such as cell engineering, genetic engineering, etc.

According to a fourth embodiment of the present invention, there is provided a method for preparing a specimen, comprising a first step of magnetically labeling a specimen to form a magnetic-labeled specimen, a second step of applying gradient magnetic field to the magnetic-labeled specimen to guide the specimen onto the surface of a grid for use in electron microscopic observation, and fixing the specimen on the grid, and a third step of subjecting the magnetic-labeled specimen on the grid to negative staining in the gradient magnetic field.

According to a fifth embodiment of the present invention, in order to facilitate the screening of specimens, an antibody specific to the specimen may be added to a specimen suspension to coagulate the specimen prior to the magnetic labeling of the specimen.

According to a sixth embodiment of the present invention, when concentration and purification of specimens is particularly desired, a step of concentrating and purifying the specimen may be added in which a gradient magnetic field is applied to the specimen suspension containing the magnetic-labeled specimen to locally concentrate only the magnetic-labeled specimen onto the surface of the suspension or water surface, and thereafter a thin tube is inserted to the position of local concentration to recover the magnetic-labeled specimen. After the concentration and purification step, the step of guiding and fixing is performed in the same manner as described above.

According to a seventh embodiment of the preset invention, the grid may be held on a detachable film through which a gradient magnetic field is applied from the reverse side of the film such that the magnetic potential at the grid portion is the highest, thus guiding and fixing the magnetic-labeled specimen onto the surface of the grid.

According to an eighth embodiment of the present invention, a device for preparing a specimen is provided, which comprises a vessel containing a liquid containing a magnetic-labeled immunocomplex composed or a specimen and a magnetic-micro-particle obtainable by subjecting the specimen and the magnetic micro-particle bound thereto, a local concentration mechanism for locally concentrating the immunocomplex to a predetermined position, a recovery mechanism for recovering the specimen, and a guide mechanism for guiding the specimen onto the surface of a grid for use in electron microscopic observation and fixing the specimen thereon.

According to the method and device for preparing a specimen of the present invention, the specimen can surely be guided onto the grid for use in electron microscopic observation and fixed by applying an external magnetic field since the specimen is magnetically labeled. The magnetic labeling of the specimen can be performed in two ways. One method is a direct method in which a magnetic-labeled antibody bound to an antibody such as monoclonal antibody that reacts with the specimen specifically is subjected directly to an antigen-antibody reaction with the specimen. Another method is an indirect method in which IgG antibody which reacts with the specimen specifically is added to the specimen to coagulate the specimen and then the specimen is subjected to an antigen-antibody reaction with a magnetic-labeled antibody bound to protein A that reacts with an IgG antibody. The former method, in which the objective such as a virus or a cell is collected selectively with the magnetic-labeled antibody by an antigen-antibody reaction contamination of matters other than the objective is minimum and electron microscopic observation can be performed with high reliability by screening the magnetic-labeled antibody as a marker. On the other hand, the latter method is poorer in selectivity since protein A used in preparing the magnetic-labeled antibody reacts all the IgG antibodies. However, when the objective is an ultramicro body such as virus, it is advantageous in that the objective is coagulated with an IgG antibody before screening and it is sufficient to screening only the presence of magnetic-labeled coagulates, which permits efficient electron microscopic observation.

The magnetic micro-particles used in the preparation of a magnetic-labeled antibody are preferably a ferromagnetic substance made of iron based oxides such as magnetite, transition metals or rare earth elements. They have a density higher than living organisms and are seen as black under an electron microscope, which makes it easy to confirm their presence.

Usually, specimens contain a variety of foreign matters in amounts larger than the objective matter. The foreign matters of course disturb electron microscopic observation, and one of the important objects of the preparation of specimens to be examined under an electron microscope is to purify the objective matter. Since a living organism itself does not respond to an external magnetic force, the method of the present invention in which specimens are magnetically labeled and only the objective matter is separated is advantageous for the purification of the objective matter. In the method of the present invention, a gradient magnetic field is applied as an external magnetic field which is designed so as to effect local concentration of magnetically labeled specimens contained in a suspension of specimens to concentrate the objective matter to a position of local concentration. Then, purification and concentration of the specimens can be achieved simultaneously by inserting a thin tube to the position of local concentration to recover the objective matter. The specimens are concentrated or localized onto the surface of the suspension, or water surface, in order to avoid contamination of foreign matters other than the objective matter as far as possible. For example, if the bottom of the vessel is selected as a position of local concentration, contamination of foreign matter, sedimented cells, etc. will be unavoidable.

The purified and concentrated specimens are then mounted on a grid for use in electron microscopic observation having a diameter of usually about 3 mm, and stained to facilitate the observation. In the conventional procedures, generally, specimens are dropped and stick onto a copper grid on which a support membrane of formyar etc. is attached, and then excessive specimens are removed using filter paper, followed by staining with phosphotungstic acid or a like staining liquor, removing the staining liquor with filter paper and natural drying. The thus-stained specimens are then subjected to electron microscopic observation. Removal of specimens and staining liquor with filter paper or a like results in absorption with filter paper of most of the part of the specimen dropped down on the copper grid and only a small portion of the specimen added remains on the grid. This is one reason why the concentration or population of virus to be examined under an electron microscope must in practice be not lower than 100,000,000 individuals/mi. On the contrary, according to the method of the present invention, specimens can be guided and fixed in the center of the surface of the grid for electron microscopes by applying, from the reverse side of a film holder for holding a grid detachably, a gradient magnetic field such that the magnetic field of the central portion of the grid is the highest. Therefore, when excessive specimen and staining liquor are removed with filter paper, the magnetic-labeled specimen is magnetically adsorbed on the grid and will not be absorbed with filter paper, etc. When observing virus particles, this permits electron microscopic observation of a very dilute specimen containing virus in the order of several tens individuals/ml, for example, with ease.

Thus, using the device for preparing a specimen according to the present invention, the method for preparing a specimen according to the present invention can be practiced with ease.

The method for preparing a specimen according to the present invention ensures accurate guidance and fixation of specimens by an external magnetic field onto the grid for electron microscope since the specimens are magnetically labeled by an antigen-antibody reaction with the magnetic-labeled body, which improves the detection sensitivity for specimens significantly. Also, with the device for preparing a specimen according to the present invention a series of steps of preparing specimens can be performed efficiently and with ease. Although the foregoing explanation has been centered on the case where influenza virus is used, the methods of the present invention are not limited to the preparation of virus but it can also be applied to electron microscopic observation of various cells such as cancer cells and lymphocytes.

In addition, the methods of the present invention can be applied not only to a method in which specimens are negative-stained on a grid but also to a method in which specimens are embedded in a resin followed by microtoming, and performing observation under electron microscope. Conventionally, when preparing a thin section, fixation, dehydration and embedding procedures are operated while repeatedly centrifuging for the sedimentation of the specimen. In contrast, according present invention, fixation of the specimen and its dehydration with an alcohol can be carried out with ease since it is possible to guide and localize the specimen to a desired position and hold it there in a gradient magnetic field instead of centrifuging. The specimen can be localized also upon embedding, and therefore, cutting or slicing the specimen with a microtome is facilitated.

As in the eighth embodiment described above, the present invention enables direct detection of unknown, unculturable virus even in a very small amount, which greatly adds to the development of virology. For example, the present invention contributes to the finding or screening of non-A and non-B hepatitis viruses. It is also useful for early diagnosis of a cellular level, such as diagnosis of cancer cells, etc., and permits observation of cancer cells which are in the stage of metastasis.

According to a ninth embodiment of the present invention, there is provided a method for preparing a specimen, which comprises a step of injecting a specimen to a magnetic-labeled body holding position at which a magnetic-labeled antibody composed of a magnetic micro-particle and an antibody or antigen bound to the magnetic micro-article is held localized by means of an external magnetic force, to subject the specimen and the magnetic-labeled body an antigen-antibody reaction, and a step of recovering the magnetic-labeled body by releasing the application of the external magnetic force, wherein the holding of the magnetic-labeled body is performed by magnetizing a magnetic member inserted in the inside the reactor, and the recovery of the magnetic-labeled specimen is performed by demagnetization of the magnetic member.

According to a tenth embodiment of the present invention, the magnetization of the magnetic member is performed in a gradient magnetic field in order to ensure accurate holding of the magnetic-labeled body to the magnetic-labeled body holding portion, and the recovery of the magnetic-labeled body is performed by the demagnetization of the magnetic member in combination with vibration of the magnetic member to forcedly release the complex composed of the specimen and the magnetic-labeled body magnetically adsorbed on the surface of the magnetic member in order to ensure the recovery of the magnetic-labeled body.

According to an eleventh embodiment of the present invention, the antigen-antibody reaction between the specimen and the magnetic-labeled body is performed with circulating the specimen through the magnetic-labeled body holding portion in order to ensure reaction of a small amount of the specimen with the magnetic-labeled body.

According to a twelfth embodiment of the present invention, the antigen-antibody reaction between the specimen and the magnetic-labeled body is performed with vibrating the magnetic member.

The method for preparing a specimen according to the present invention in which magnetic micro-particles, which are micro-particles of a magnetic substance, are used in labeling an immune reaction, the magnetic-labeled body is guided to the magnetic-labeled body holding portion by means of the gradient magnetic field generating mechanism, and magnetically adsorbed on the magnetic member inserted in the inside of the magnetic-labeled body holding portion.

In order to efficiently label a minute amount of the specimen magnetically with the magnetic-labeled body, it is advantageous to broaden area where antigen-antibody reaction takes place as far as possible. Therefore, the magnetic member may preferably be made of a thin wiring of a soft magnetic material wound in a form of coil, for example, so that the surface area of the magnetic member can increase as broad as possible. As for the soft magnetic material for wiring, materials having a high permeability which show low residual magnetization are suitable. Examples of the high permeability material which can be used include nickel, pure iron, permalloy, amorphous alloys, etc. The diameter of the thin wiring ranges preferably 20 μm to 1 mm, and more preferably 50 μm to 0.2 mm. However, the present invention is not limited thereto.

When the magnetic member is magnetized from outside by means of a magnet, a magnetic field of a steep gradient is generated around each wiring resulting in that the magnetic-labeled body is magnetically adsorbed on the surface of each wiring. Therefore, the higher the density of the wiring, the more the magnetic-labeled body can be held in the magnetic-labeled body holding portion.

It is more advantageous that the magnetic field generated by the magnet is higher. On the other hand, this causes enlargement of the device. It is therefore suitable to use magnets with magnetic field in the order of several kG to several tens kG. The magnet may be an electromagnet or a permanent magnet.

The provision of the magnetic-labeled body holding portion in a part of the reactor which part is of a constricted form leads to reduction in magnetic gap distance, thus permitting miniaturization of the magnet. This method is also advantageous for guiding the specimen to the magnetic member and increasing the possibility of contact between the specimen and the magnetic-labeled body. The most advantageous method for increasing the possibility of contact between the specimen and the magnetic-labeled body is to circulate the specimen by a pump, for example. The rate of circulating the specimen may vary depending on the amount of the specimen, strength of the magnetic field, the density at which the magnetic member is charged, etc. but it is preferred to circulate the specimen at a rate of 1 ml to 100 ml per hour.

Another effective method for increasing the possibility of contact between the specimen and the magnetic-labeled body is to perform an antigen-antibody reaction with gently vibrating a group of wirings of a magnetic substance. By gently stirring the suspension containing the specimen, the period of time required for magnetic labeling can be reduced.

According to the present invention a minute amount of specimen can be labeled magnetically efficiently and accurately so that the mount of magnetic-labeled body, which has been a large excess in the conventional methods, can be considerably reduced, for example, to a level one tenth or less. In addition, it is possible according to the present invention to perform screening or collection of virus in a dilute solution in which only a few individuals per ml.

After the above step, it is important to completely recover the specimen which is bound to the magnetic-labeled body. For this purpose, the magnetic member has to be demagnetized. The most complete demagnetization method is to use as a magnetic member a high permeability material having residual magnetization to remove the magnetic field of the magnet. To be most simple, a permanent magnet having a large magnetic energy product such as a rare earth element magnet is used and the permanent magnet or the reactor is made movable, thus ensuring application and removal of magnetic field. When an electromagnet is used as a magnet, care must be taken for the demagnetization of the core of the electromagnet. Since it is often the case that the magnetic-labeled body sticks on the surface of the magnetic member even after removing the magnetic field a large amount of washing liquor or recovering liquor would often be needed. In the present invention efficient recovery of the magnetic-labeled body is achieved by mechanically moving the magnetic member in a small amount of recovering liquor.

By vigorously vibrating the magnetic member, the magnetic-labeled body sticking to the magnetic member can be released. The frequency of vibration is by one digit shorter than that of vibration at the time of accelerating antigen-antibody reaction. It is preferred to perform vibration at a frequency of 10 to 60 Hz, for example.

As stated above, the method for preparing a specimen according to the present invention can be performed.

After the preparation of specimens according to the present invention the specimen obtained can be determined for the detection of a very small amount of antigens or antibodies using the laser magnetic immunoassay methods and apparatus described above.

According to a thirteenth embodiment of the present invention, there is provided a device for preparing a specimen, comprising a device for preparing a specimen, comprising a reactor, a magnetic-labeled body holder provided with the reactor for holding a magnetic-labeled body composed of a specimen and a magnetic micro-particle bound to the specimen, a magnet provided with the magnetic-labeled body holder and placed outside the reactor, a gradient magnetic field generating mechanism provided with the magnet for generating gradient magnetic field, a magnetic member placed inside the reactor, a specimen circulation mechanism for circulating the specimen, and a recovery mechanism for recovering the magnetic-labeled specimen, the recovery mechanism comprising a mechanism for giving relative movement to the magnet and the magnetic-labeled body holder to release the magnetic force applied to the magnetic-labeled specimen.

In order to make sure to recover the specimen, it is preferred that the magnetic member is movable and the specimen recovery mechanism is provided with a mechanism for forcedly release a complex between the magnetic-labeled body magnetically adsorbed on the magnetic member and the specimen after release of the magnetic force.

In the methods according to the ninth to twelfth embodiments of the present invention, it is designed that the specimen passes around the magnetic member on which the magnetic-labeled body is held, the chance of contact or encounter between the specimen and the magnetic-labeled body increases, in contrast to the conventional methods for the preparation of specimens for RIA etc. in which a large excess amount of a standard reagent is added to the specimen solution in order to increase the possibility of contact between the specimen and the reagent. Since the reduction in the amount of the label substance (magnetic-labeled body) to be added by about one digit is possible the present invention is advantageous in reducing the occurrence of non-specific reaction due to unreacted magnetic-labeled body. As the result the S/N ratio upon measurement is improved, which is very effective to improve the detection sensitivity. Since expensive antibodies such as monoclonal antibodies can be used effectively, economization is possible in practicing the invention.

Furthermore, the present invention is also advantageous in the detection of virus which is present in a very limited amount in a large amount of specimen such as gargling water from a patient since the specimen can be reacted continuously or sequentially. The method of the present invention is suitable for automation. In addition, non-magnetic particles and magnetic micro-particles used as a label cause no problem with respect to radioactivity and toxicity to humans, and therefore those stable to specimens can be obtained with ease and safely, which is additional advantage of the present invention.

The ninth to twelfth embodiments of the present invention can be applied not only to detection of virus but also to early diagnosis of cancers, tests for allergy, bacteria, etc., measurement of various hormones such as peptide, hormones, or various enzymes, vitamins, or drugs, which measurement has heretofore been performed by RIA. Therefore, accurate measurement which has been impossible to perform unless RIA is used in a limited installation can be performed widely in a more general environment, which makes it possible to practice effective therapy at early stages.

Furthermore, the present invention according to the ninth to twelfth embodiments can be applied to the separation and removal of virus from dedicated blood as well as to various immunological diagnosis. That is, use of the magnetic micro-particles as a label substance makes it possible to specifically catch and remove virus which is bound to the magnetic-labeled body by an antigen-antibody reaction in dedicated blood by an external magnetic force. Although the heretofore explanation has been made with reference to influenza virus as a model, if appropriate choice of magnetic-labeled body is made depending on the kind of virus, any virus can be separated and removed by the present invention. Using a mixture of a plurality of magnetic-label bodies, AIDS virus, ATL virus, non-A and non-B hepatitis viruses can be removed simultaneously from dedicated blood. In addition, non-A and non-B hepatitis viruses which have not yet been confirmed for their presence can be removed if IgG is isolated from the serum of a patient suffering non-A and/or non-B hepatitis or immunized chimpanzee and magnetic-labeled antibody is prepared therefrom.

In addition, the thirteenth embodiment of the present invention is effective not only for the separation and removal of the above-described viruses but also for the purification of viruses. For example, if it is intended to find unknown virus, it is often the case that contaminants such as various proteins and the like substances disturb electron microscopic observation. Contaminants other than virus cause problems in the case of preparation of vaccines, because they are reasons for side effects of vaccines. On the other hand, when the device of the present invention is used, the objective virus is caught with the magnetic-labeled body and magnetically adsorbed on the surface of the magnetic member, and therefore, virus can be purified by releasing magnetic force and recovering virus after washing off the adsorbing virus. The magnetic-labeled body bound to virus can be released with ease by rendering the liquid or medium acidic in the order of 3 to 4.

The present invention can be used for catching a cancer marker, and a very minute amount of cancer cells freed from the cancer tissue and is in as stage of metastasized to body fluid such as blood as well as virus. Therefore, the present invention is also effective for the early diagnosis of cancer cells on the level of cells. Furthermore, a minute amount of physiologically active substances such as enzymes, hormones, etc. which bind specifically by an antigen-antibody reaction can be caught by the present invention.

According to the fourteenth embodiment of the present invention, there is provided a method for preparing a specimen, comprising a first step of magnetically labeling a specimen in a suspension containing the specimen a second step of performing local concentration of the specimen by applying a gradient magnetic field to the suspension, wherein the specimen is concentrated to a predetermined position on or in the vicinity of the surface of the suspension, and a grid for use in electron microscopic observation is inserted to the position of local concentration to recover the specimen on the grid.

The first step of this embodiment can be performed, for example, by binding the magnetic-labeled body to the specimen by an antigen-antibody reaction. The magnetic microparticles used in the magnetic-labeled body may preferably be a ferromagnetic substance such as an iron based oxide such as magnetite, transition metal or rare earth elements.

According to a fifteenth embodiment of the present invention, a gradient magnetic field is applied to the suspension from the side of the grid opposite to the side on which the magnetic-labeled specimen is recovered such that the magnetic field is the highest at the position of the grid to guide and fix the magnetic-labeled specimen to the grid.

Upon recovering the specimen on the grid, either the vessel containing the specimen suspension or the grid may be moved. When it is desired to further purify the specimen directly fixed onto the grid by magnetic adsorption or attraction good results will be obtained by repeating operations of immersing the grid in the vessel in which washing liquor is injected under application of magnetic field and then taking it out therefrom. With the washing thus performed, impurities which are not adsorbed magnetically can be removed while the magnetic-labeled specimen remains fixed to the grid.

The thus concentrated and purified specimen can be stained, if desired, so that electron microscopic observation can be performed with ease. It is preferred to perform the staining operation by immersing the grid on which the specimen is fixed in the vessel in which a staining liquor such as phosphotungstic acid etc., and withdrawing therefrom after a predetermined period of time under application of magnetic field.

The specimen on which the preparation has thus completed is subjected to electron microscopic observation.

In practicing the method for preparing a specimen for electron microscopic observation, it is advantageous to use a device for preparing a specimen for electron microscopy, comprising a gradient magnetic field generating mechanism for generating a gradient magnetic field, a grid holder for holding a grid for use in electron microscopic observation (grid holder) at a position at which the gradient magnetic field is concentrated, and a guide mechanism for guiding the grid holder to the water surface in the vessel.

As for the gradient magnetic field generating device, one described in the eighth embodiment of the present invention, may be used. That is, a device can be used which comprises a specimen container placed above an electromagnet, a pole piece in the form of a pencil and having a tip diameter as large as the diameter of a grid, the pole piece being arranged vertically just above the surface of water in the specimen container, the pole piece opposing the electromagnet. Since the magnetic flux radiated from the electromagnet concentrates to the pencil-form pole piece, the magnetic field is the highest just below the pole piece.

As for the grid holder, a grid stage made of a non-magnetic substance so constructed as to be fitted to the tip of the pencil-form pole piece can be used advantageously. The grid can be mounted on the grid stage, for example, using a double-sided adhesive film which can be pressed and adhere on one side to the grid stage on the other side of which may be fixed the grid.

In the fourteenth embodiment described above, the specimen is concentrated on or in the vicinity of the surface of the specimen suspension and the grid is inserted to the position of local concentration to recover a specimen from the specimen suspension containing only a minute amount of the specimen, the objective matter, but instead much foreign matters, which makes it possible to efficiently recover the specimen in the same condition as purified one. Therefore, the method for preparing a specimen according to the present invention permits a drastic increase in the detection sensitivity of electron microscopic observation. In addition, the method of the present invention is very simple to operate, which makes more efficient a series of steps for preparing a specimen.

In the fifteenth embodiment of the present invention, the operation of preparation can be carried out smoothly by applying a gradient magnetic field to the specimen suspension from the reverse side of the grid such that the magnetic field is strongest at the position of the grid to guide and fix the magnetic-labeled specimen to the grid.

According to a sixteenth embodiment of the present invention, the method for preparing a specimen can be performed efficiently using a device for preparing a specimen, composing a mechanism for generating gradient magnetic field, a grid holder for holding a grid for use in electron microscopic observation at a position where gradient magnetic field is concentrated, and a guide mechanism for guiding the grid holder to a predetermined position of the surface of the suspension contained in a vessel.

As described above, according to the fourteenth to sixteenth embodiments of the present invention, it is possible to directly detect unknown, unculturable virus even in a minute amount, which contributes to the development of virology. For example, the present invention can contribute to finding non-A and non-hepatitis. Furthermore, the present invention is effective for the early diagnosis of cancer cells, etc. on a cellular level, and it makes it possible to observe a minute amount of cancer cells which are released from cancer and metastasized into a body fluid such as blood.

According to the fourteenth to sixteenth embodiment of the present invention, only the magnetic-labeled specimen is guided and gathered to the point where the magnetic field is the strongest when a gradient magnetic field is applied to the specimen suspension containing the magnetic-labeled specimen.

Although the specimen suspension contains besides the objective matter living organisms as foreign matters in larger amounts, the living organisms do not respond to external magnetic force, resulting in that only the magnetic-labeled specimen is guided to the position of local concentration.

Since the position of local concentration is set up on or in the vicinity of the surface of the specimen suspension, contamination of foreign matters and cells which have settled on the bottom of the vessel can be avoided. This further reduces contamination of matters other than an objective matter. As the result, the specimen is in the same condition as being purified.

Inserting the grid for use in electron microscopic observation at the position where the magnetic-labeled body is concentrated locally, the magnetic-labeled specimen adhere to the surface of the grid, resulting in that a large amount of purified specimen can be recovered on the grid.

Since the magnetic micro-particle in the magnetic-labeled body thus recovered has a density higher than living organisms, the magnetic micro-particles be seen as black under the view of the electron microscope so that their presence can be confirmed very easily.

In addition, in the method for preparing a specimen for use in electron microscopic observation, the specimen is recovered on the grid by inserting the grid to the position of local concentration of the magnetic-labeled body localized by the application of a gradient magnetic field, and when further purification or staining of the specimen is desired subsequent to the operation of the recovery, the subsequent operations can be performed-with ease in the condition where a gradient magnetic field is still applied to the grid. The application of gradient magnetic field to the grid on which the specimen is recovered, loss of the specimen thus recovered can be prevented during purification or staining, resulting in further improvement in the detection sensitivity. For example, a dilute specimen such as one containing virus in a population in the order of several tens individuals per ml can be detected.

EXAMPLES

Referring to the attached drawings and examples the present invention will be described in greater detail but it should not be construed as being limited thereto.

Example 1

FIG. 1 shows an example of the device for collecting a specimen according to the first embodiment of the present invention, in which reference numeral 1 indicates a test vessel, 2 an antigen-antibody complex (or immunocomplex) containing a specimen to be detected or determined, 3 a magnetic piece, 4 a winch or windlass, 5 an electromagnet, 6 a pole piece, and 7 a yoke, In this example, a gradient magnetic field generating device includes the electromagnet 5, the pole piece 6 and the yoke 7. The magnetic flux going out from the electromagnet 5 passes through the test vessel or specimen container 1 and is gathered by the pole piece 6, and goes back to the electromagnet via the yoke 7, thus forming a magnetic circuit. The pole piece 6 having a sharp tip with a cross-section sufficiently smaller than that of the electromagnet 5 is arranged just above the test vessel 1 to form at gradient magnetic field such that the magnetic flux is concentrated to the pole piece 6. For this purpose, in this example, the diameter of the electromagnet 5 is set up to be 100 mm, and the diameter of the pole piece 6 is set up to 8 mm, with the tip of the pole piece being conical, and the pole piece 6 is arranged just above the surface or level of the liquid contained in the test vessel with a height from the surface of the liquid of 10 mm. The pole piece 6 is provided with a through hole of a diameter of 0.2 mm in the central portion in the cross-section along the length thereof. In the through hole, a thin nickel wire 3 having a diameter of 50 μm made of a ferromagnetic substance is inserted which is movable vertically by means of the winch 4. The immunocomplex concentrated on the liquid surface just below the pole piece 6 is magnetically adsorbed on the magnetized, thin nickel wire 3 by inserting the wire 3 into the solution in the test vessel, and thereafter taking out the wire 3 above the liquid surface to collect the specimen. After collection, the tip of the wire is cut off, and the tip is inserted the sample chamber of an electron microscope for observation of the surface of the nickel wire 3. As the result, the objective specimen was observed.

When the device for collecting a specimen was used for collecting influenza virus, electron microscopic observation of a dilute specimen containing virus in population in the order of 10 individuals/ml was successful for the first time. As is well known, it is necessary to cultivate virus in an egg to a population in the order of 1,000,000 individuals/ml.

The magnetic piece 3 is not limited to thin nickel wire but a thin wire or film of a ferromagnetic substance can be used as a collector. Instead of taking up the magnetic piece 3, the magnetic piece 3 may be fixed to the pole piece 6 and the pole piece 6 together with the magnetic piece 3 may be move up and down. Alternatively, the magnetic piece 3 may be fixed and the test vessel 1 may be moved up and down.

Example 2

Anti-Ishikawa rabbit immuneserum (type A influenza virus) fixed on the surface of non-magnetic particles made of acrylic polymer having a diameter of 1 μm and gargling water from a patient were allowed to reacted at 35° C. for 2.5 hours. Then, after adding magnetic-labeled antibody composed of anti-lshikawa-ferrate IgG IgG, the reaction was continued for another 2.5 hours at 35° C., followed by centrifuging at a speed of 1,500 rpm for 5 minutes to precipitate only the non-magnetic particles entirely. The precipitate was placed in the test vessel 1 shown in FIG. 1 and after dilution with 1 ml of PBS solution (phosphate buffer saline solution), the specimen was collected in the same manner as in Example 1, followed by electron microscopic observation. As the result, type A influenza virus was detected successfully.

Example 3

After activating the surface of non-magnetic particles made of acrylic polymer having a diameter of 1 μm in order to facilitate the adsorption of virus, gargling water from a patient was added and the mixture was allowed to react at 35° C. for one night. Thereafter, anti-Singapore fenate IgG (type B influenza virus) was added and the mixture was allowed to react at 35° C. for 2.5 hours, followed by centrifuging at 1,500 rpm for 5 minutes to precipitate only the non-magnetic particles entirely. The precipitate obtained charged in the test vessel 1 in the device shown in FIG. 1. After dilution with 1 ml of PBS solution (phosphate saline buffer solution), the specimen was collected in the same manner as in Example 1, and subjected to electron microscopic observation. As the result, type B influenza virus was detected successfully.

Example 4

Figure 2:
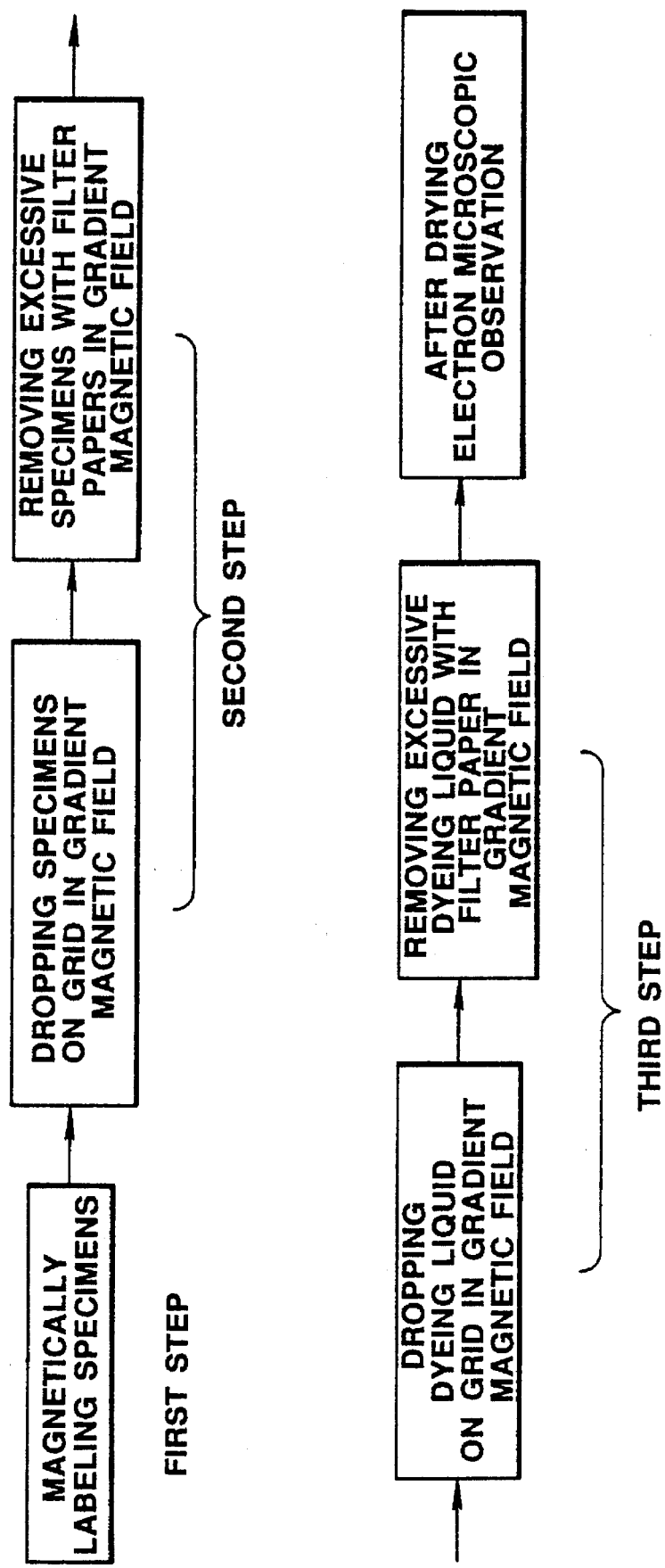
FIG. 2 is a diagrammatic flow chart of a method for preparing a specimen to be examined with an electron microscope according to one embodiment of the present invention.

FIG. 2 is a diagrammatic flow chart illustrating an example of the method for preparing a specimen according to the fourth embodiment of the present invention, in which the first step is a step in which a specimen is magnetically labeled, the second step is a step in which the magnetic-labeled specimen is guided and fixed to a grid for use in electron microscopic observation in gradient magnetic field, and the third step is a step in which negative staining is performed in gradient magnetic field. The specimen used in this example is type A influenza virus (A/Ishikawa/7/82(H3N2)). It was confirmed that the specimen contained virus in a population of 1,000,000 individuals/ml as the result of blood coagulation reaction and blood cell calculating plate. The influenza virus of this concentration was serially diluted with PBS solution at a dilution ratio of 1/10 the original, and a limit for electron microscopic observation was tested. At first, the specimen was observed under electron microscope in the conventional manner without magnetically labeling the specimen, which failed to confirm presence of virus.

Referring to the first step of this example, the antibody used for magnetic labeling is IgG obtained by purifying rabbit hyperimmune antiserum to virus. This was bound by covalent bonding to a dextran-coated magnetic micro-particle of magnetite having an average particle size of 10 nm to obtain magnetic-labeled antibody. The labeling of the specimen was performed by incubating 1 ml of the specimen and 10 μL of the magnetic-labeled antibody at 35° C. for 2.5 hours.

Figure 3:
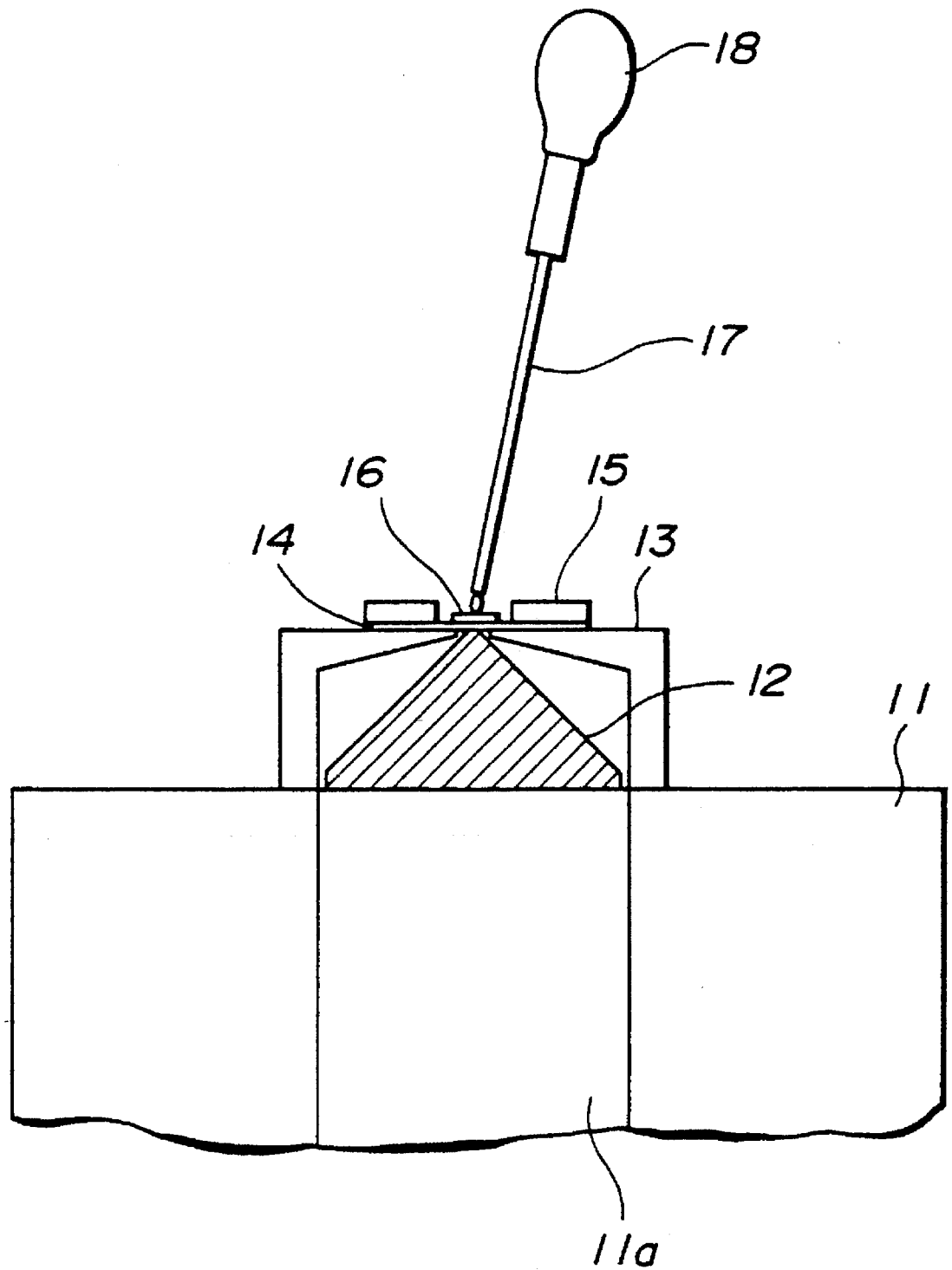
FIG. 3 is a schematic cross-sectional view of a device for guiding and fixing a magnetic-labeled specimen onto a grid for electron microscopic observation.

Now reference is made to the second step of this example. FIG. 3 is a cross-sectional view of a device for guiding and fixing the magnetic-labeled specimen on to a grid for use in electron microscopic observation in gradient magnetic field, in which reference numeral 11 is an electromagnet, 11a an iron core for the electromagnet, 12 a pole piece, 13 stage for mounting a grid, 14 an adhesive film, 15 a grid holder. 16 a grid, 17 a thin tube, and 18 a cap.

The pole piece (A) 12 made of pure iron and having a conical shape is mounted on the iron core 11a of the electromagnet, and is covered with the grid stage 13 of aluminum for mounting grid. The tip of the pole piece (A) 12 is cut off so as to avoid concentration of magnetic field excessively, and the diameter of the tip end is 2 mm. In this example, the electromagnet was energized so as to give magnetic field of about 3 kG at the end surface of the pole piece. The grid stage 13 is formed with a through hole of 4 mm in diameter in the center thereof, with the end surface of the pole piece (A) 12 being positioned in the center of the through hole, and 0.5 mm below the surface of the grid stage. The through hole is not mandatory. However, it was provided in this example because a strong magnetic field was obtained easily, and alignment between the grid 16 and the pole piece (A) 12 was easy. The copper grid of 3 mm in diameter on which was attached Formvar support member was weakly bonded lightly to a parafilm having adhesiveness (adhesive film) so as to be detachable, and was supported by the grid holder 15. The grid holder 15 was made of an acrylic resin and had a size of 20 mm in outer diameter, 8 mm in inner diameter, and 1 mm in thickness as shown in FIG. 3. On the bottom, the above-described adhesive film 14 was stuck. Since the grid 16 was small, great care must be taken for handling the grid. However, if handled as contained in the grid holder 15 as in this example, preparation of specimens becomes easy, and in addition, transportation and storage of the grid 16 after completion of the preparation of specimens is also easy. When the grid 16 is to be taken out, the adhesive film 14 on the reverse side may be put lightly with one's finger, the grid 16 will be easily stripped off from the adhesive film 14, and the grid 16 can be put out with a pincette.

When the grid holder 15 was mounted on the grid stage 13 in the center thereof, and a magnetic-labeled specimen in the capillary tube 17 was dropped on the grid 16 in an mount of several μl by compressing the cap 18, with the electromagnet 11 being energized, a gradient magnetic field was generated such that the central portion of the grid was the highest by means of the pole piece (A) 12, resulting in that the magnetic-labeled specimen was guided to the central portion of the grid 16 and magnetically adsorbed thereon accurately. About one minute after dropping the specimen, excessive specimen was removed with filter paper while the electromagnet remained to be energized. With these operations, only the magnetic-labeled specimen was fixed onto the grid 16.

In the third step of this example, while keeping the electromagnet 11 energized, several μl of negative staining liquid composed of 1% phosphotungstic acid (pH 7) was dropped onto the grid 16, and after 30 seconds excessive staining liquor was removed with filter paper and dried naturally.

Figure 4:
FIG. 4 is an electron micrograph showing image of influenza virus obtained according to a method for preparing a specimen described in Example 1.

The above-described method for preparing a specimen for electron microscopic observation was applied to the determination of influenza virus to examine the detection limit, and as the result screening of virus was successful with the range of vision of electron microscope at a magnification of 50,000 times even when the concentration of the virus was 10,000/ml with ease. FIG. 4 is an electron micrograph of magnetic-labeled influenza virus. The diameter of the virus was 100 nm, and it will be apparent from FIG. 4 that the magnetic-labeled antibody showing black was bound to the virus.

Example 5

A step of coagulating virus was performed prior to the step of magnetically labeling the specimen described in Example 4. That is, 1 ml of the specimen used in Example 4 was mixed with 20 μl of the IgG antibody and the mixture was incubated at 35° C. for 2.5 hours and sequentially at 4° C. for one night to coagulate virus. Further, the immunocomplex composed of the virus and IgG antibody was also precipitated by centrifuging at 3,000 rpm for 30 minutes, and the precipitate was dispersed again in PBS solution.

Figure 5:
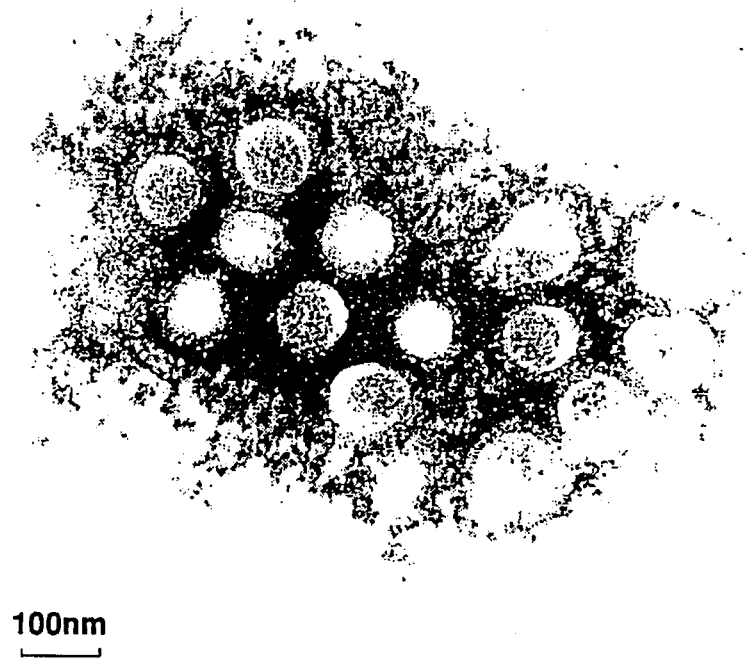
FIG. 5 is an electron micrograph showing image of influenza virus obtained according to a method for preparing a specimen described in Example 2.

After this step, the same step of preparing a specimen as in Example 4 was repeated except that different magnetic-labeled antibody was used. That is, in this example, the dextran-coated magnetic micro-particle was bound to protein A. Since protein A binds specifically with IgG antibody, the virus coagulated with the IgG antibody was magnetically labeled. Thus, application of pretreatment to coagulate virus particles to each other further facilitated electron microscopic observation, and screening was successful with virus concentration in the order of several thousands individuals/ml with ease. FIG. 5 is an electron micrograph of magnetically labeled virus. It is apparent that ten and some virus particles coagulated and the magnetic-labeled antibody showing black was bound to the periphery of the viruses.

A method in which specimens are coagulated prior to electron microscopic observation to facilitate the observation has been known as immuno-electron microscopy. The present invention which as far as the present inventors know uses magnetically labeling specimens for the first time has improved detection sensitivity by 5 digit or more as compared with the conventional immuno-electron microscopy.

Example 6

After the first step of coagulating virus and magnetically labeling specimens described in Example 5, a step of concentrating and purifying the specimen was performed, followed by practicing the second and third steps in Example 5. The step of concentrating and purifying will be described in detail below.

Figure 7B:
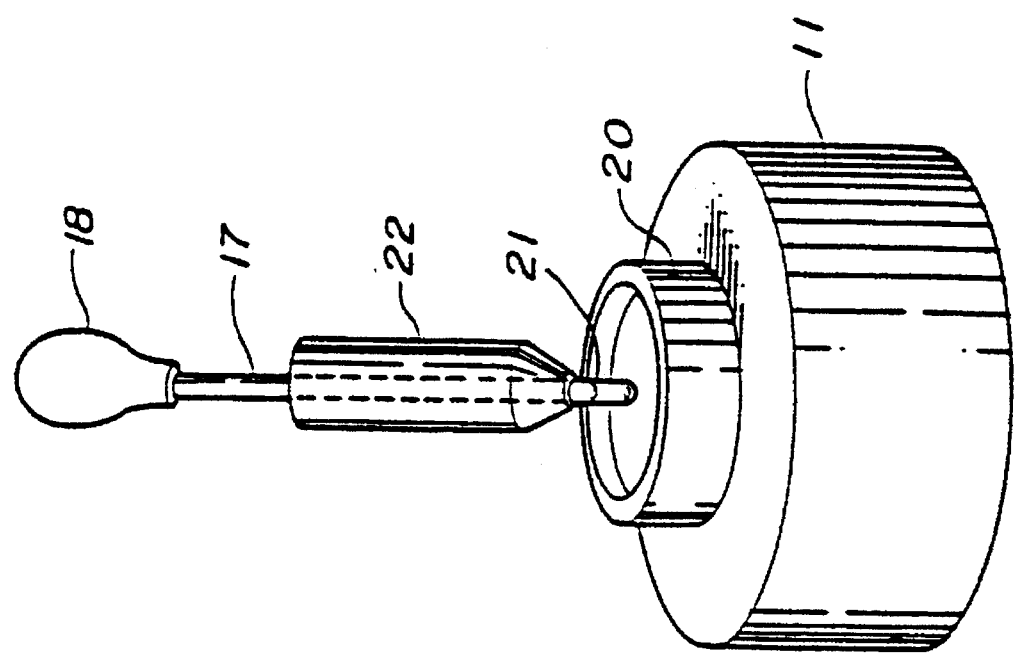
FIG. 7 is a schematic illustration of a step of concentrating and purifying a specimen and a step of recovering the specimen, in which (a) indicates the step of concentration and purification, and (b) indicates the step of recovering the specimen.
Figure 7A:
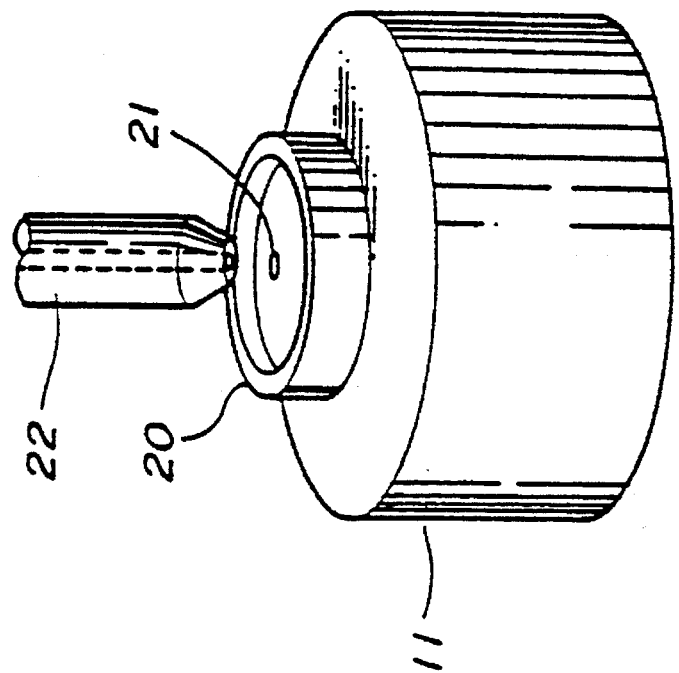

FIG. 7 (a) and 7 (b) illustrate the step of concentrating and purifying the specimen FIG. 7 (a) illustrates the step of concentrating and purifying, and FIG. 7 (b) the step of recovering the specimen.

In FIG. 7, reference numeral 20 indicates a vessel, 21 a magnetic-labeled specimen, 21-1 a recovered specimen, 22 is a pole piece (B). Since the magnetic circuit is so designed that the magnetic flux outgoing the electromagnet 11 is concentrated to the pole piece (B) 22, gradient magnetic field is generated such that the magnetic field on the surface of the liquid contained in the vessel just below the pole piece (B) 22 is the highest. In this example, the highest magnetic field was 8 kG. The center of the pole piece (B) 22 was hollow so that the capillary tube 17 was able to be inserted therein. In the vessel 20, there was contained 1 ml of the specimen suspension containing the magnetic-labeled specimen 21 after the first step.

In the step of concentrating and purifying (a), the vessel 20 was inserted between the electromagnet 11 and the pole piece (B) 22. When the electromagnet was energized, the magnetic-labeled specimen 21 was guided to the water surface just below the pole piece (B) 22 and concentrated there. In this case, since various contaminants present in the specimen suspension do not respond to magnetic force, only the magnetic-labeled specimen 21 was present at the position of concentration, and therefore, concentration and recovery of the specimen 21 were carried out simultaneously.

In the step of recovering (b), the capillary tube was inserted in the through hole of the pole piece (B) 22 with keeping the electromagnet energized, and when the capillary tube 17 was brought in contact with the specimen, the specimen suspension was recovered in the capillary tube due to capillarity and the magnetic-labeled specimen was also recovered in the capillary tube due to magnetic attraction. In this example, the capillary tube 17 was a size of 1.1 mm in outer diameter and 0.5 mm in inner diameter was used. About 5 μl of the solution was absorbed naturally. The cap 18 was to drop the recovered specimen on the grid in the next step.

In the conventional method for preparing a specimen for electron microscopy, when the purification of the specimen is insufficient electron microscopic observation will be greatly disturbed. However, purification effect of this example facilitates electron microscopic observation and increases detection sensitivity as the result of the effect of concentration, thus enabling screening of virus in a virus concentration in the order of several hundreds individuals/ml in a short time.

The above-described method for preparing a specimen can be practiced with ease and efficiently using the device described hereinbelow.

Figure 8:
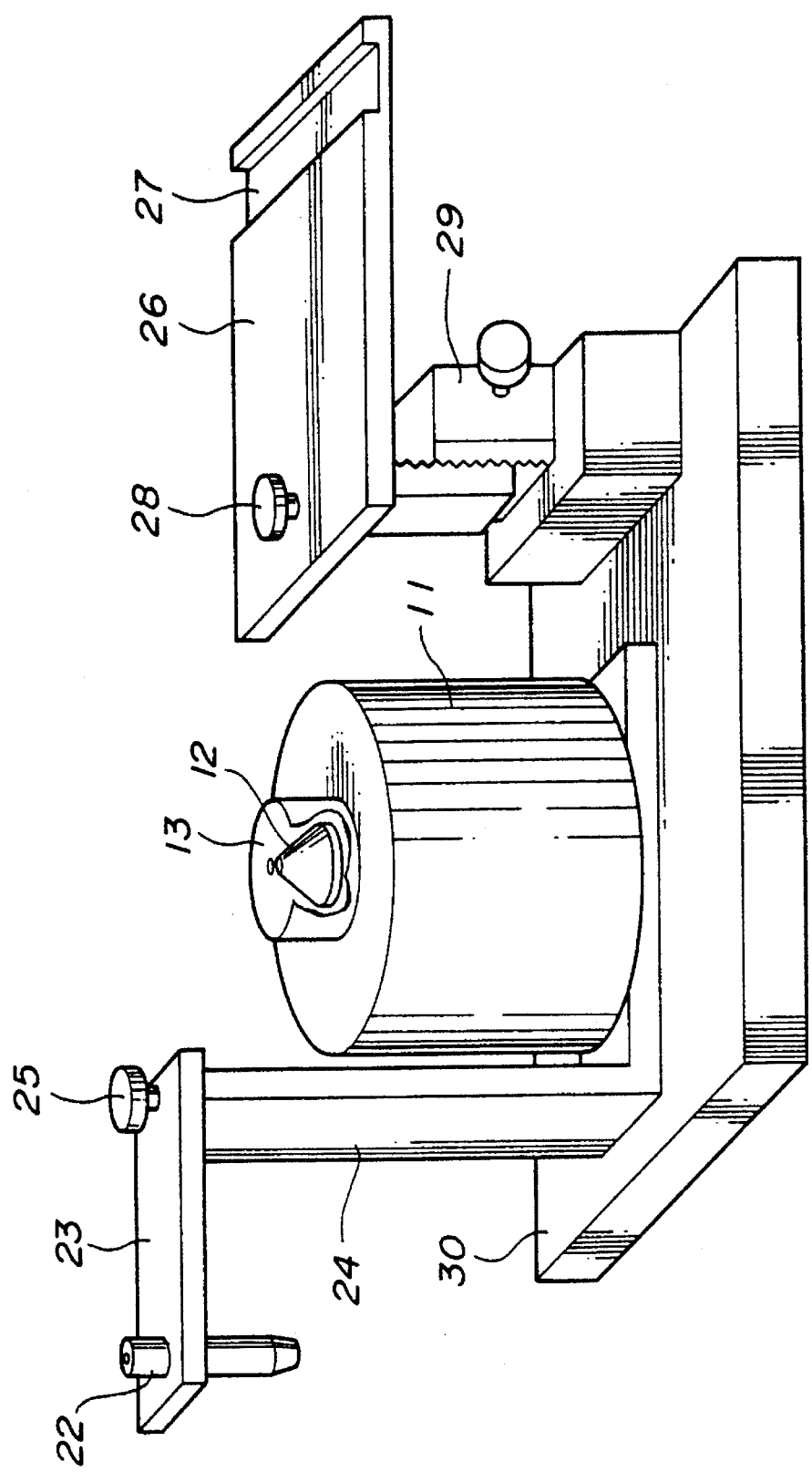
FIGS. 8 and 9 are each a schematic perspective view Of a device for preparing a specimen to be examined with an electron microscope according to one embodiment of the present invention.
Figure 9:
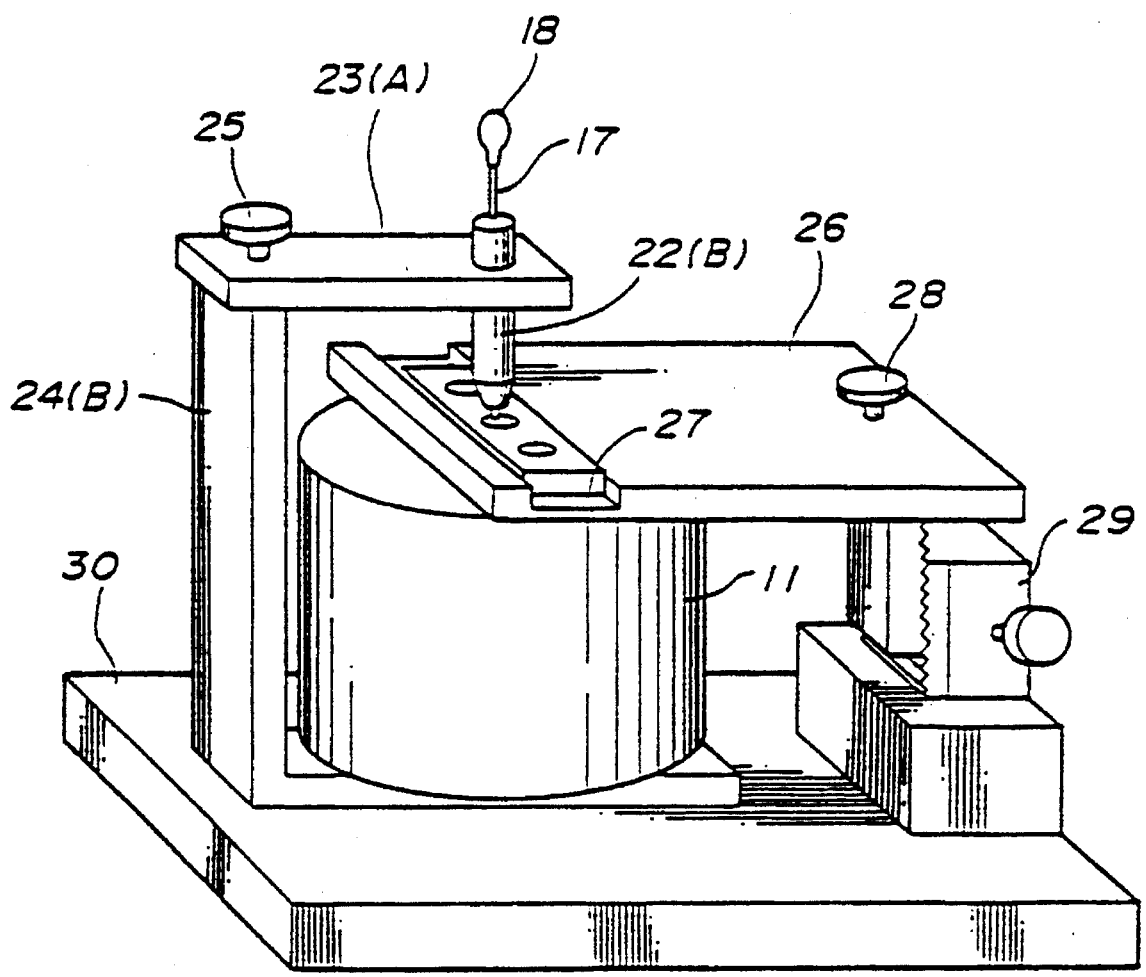

FIGS. 8 and 9 each illustrate the construction of the device for preparing a specimen for use in electron microscopic observation, in which reference numeral 23 indicates a yoke (A) for holding the pole piece (B) 22, and 24 a yoke (B). The yoke (A) 23 is linked to the yoke (B) 24 through a yoke clamp screw 25 for clamping a yoke and can fix the yoke 23 in any direction as shown in FIG. 8. The magnetic flux from the electromagnet 11 is converged by the pole piece (B) 22 after passing the vessel 20 (see FIGS. 7(a) and 7(b)), and going back to the electromagnet 11 through the yoke (A) 23 and the yoke 24 (B), thus forming a magnetic circuit. When the distance between the electromagnet 11 and the pole piece (B) 22 was 11 mm, the magnetic field generated upon application of current of 1 A to the electromagnet 11 at the position 0.5 mm just below the pole piece (B) 22 was 8 kG. The vessel 20 was set on the vessel guide face 27 provided with the vessel support 26, and was attached to a height control stage 29 with a clamp screw for clamping the stage for supporting the vessel. The platform 26 for supporting the vessel was controllable for its height to a desired height by means of the height control stage 29, and as shown in FIG. 8, the stage 26 can be fixed in any desired direction.

The above-described purification and concentration step are carried out after arranging the device of the present invention as shown in FIG. 7. Firstly, the vessel 20 containing a specimen was placed on the vessel guide face 27 in the condition in which the capillary tube 17 was withdrawn from the pole piece (B) 22, and the height of the vessel was controlled with the height control stage 29 so that the distance of the pole piece (13) 22 and the vessel 20 from the water surface was 5 mm. Then, current of 1 A was applied to the electromagnet, and the magnetic-labeled specimen was guided and concentrated to the water surface just below th pole piece (B) 22. After about 1 minute the capillary tube 17 was inserted in the through hole of the pole piece (B) 22, and the vessel was lifted upward by means of the height control stage 29 until the capillary tube 17 came into contact with the water surface in the vessel 20, the magnetic-labeled specimen together with the specimen suspension was instantaneously absorbed into the capillary tube 17 by magnetic attraction. In order to ensure the recovery of the specimen, it is preferred to repeat the operation of bringing the capillary tube 17 into contact with the water surface since the specimen is concentrated on the water surface, the specimen can be recovered most efficiently at the moment at which the capillary tube 17 comes into contact with the water surface. When the capillary tube 17 is dipped in water too much it is impossible to recover it. After 5 hours the application of current to the electromagnet 11 was stopped, the capillary tube 17 was taken out of the pole piece (B) 22, the specimen is recovered in the capillary tube 17.

Figure 6:
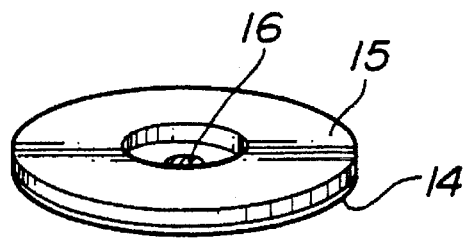
FIG. 6 is a schematic perspective view of a grid holder.

Next, the method of practicing the second and third steps using the device for preparing a specimen of this example are explained. For the second and third steps, the device is fitted as shown in FIG. 8. That is, the pole piece (B) 22 and the vessel support stage 26 above the electromagnet 11 are retreated by unfastening the yoke clamp screw 25 and the vessel support stage clamp screw 28, respectively, and turning them. The pole piece (A) 12 is mounted on the iron core 11a of the electromagnet 11 and the grid stage 13 is mounted on the pole piece 12 (A), as shown in FIG. 3. In the center of the stage.13, the grid 16 shown in FIG. 3 and FIG. 6 is mounted. Then, current of 0.5 A is applied to the electromagnet 11 to energize the electromagnet, and in this condition the specimen recovered in the capillary tube 17 is dropped. From the reverse side of the grid holder 15 is applied a gradient magnetic field such that the center of the pole piece (A) 12 is highest, and thus the magnetic-labeled specimen is adsorbed magnetically on the center of the surface of the grid 16 and fixed thereto. In this case, if the magnetic field is too strong, the formvar support membrane of the grid is broken from time to time. Therefore, it is preferred to weaken the strength of the magnetic field to a level lower than that in the concentration and purification step. In the device of this example, when the electromagnet was energized with a current of 0.5 A, the magnetic field above the grid was about 2.5 kG.

Example 7

Figures 10A, 10B, 10C, 10D, 10E:
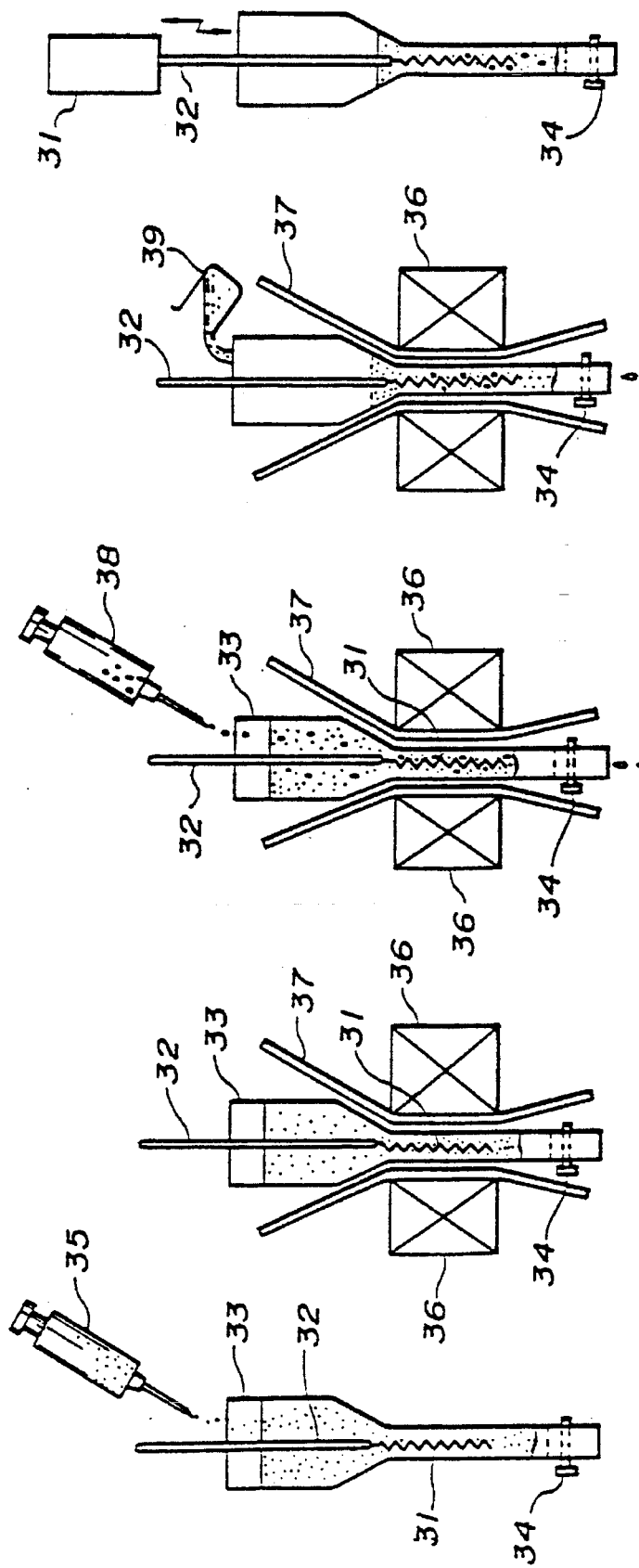
FIGS. 10(a), 10(b), 10(c), 10(d), and 10(e) illustrate procedures of preparing a specimen according to another embodiment of the present invention, in which 10(a) indicates a step of injecting a magnetic-labeled antibody, 10(b) a step of holding the magnetic-labeled antibody, 10(c) a step of injecting and incubating a specimen, 10(d) a step of washing and 10(e) a step of recovering the specimen.

FIGS. 10 (a) to 10(e) illustrate the devices for preparing specimens according to embodiments of the present invention; FIG. 10(a) indicates a step of injecting a magnetic-labeled antibody, FIG. 10(b) a step of holding a magnetic-labeled antibody, FIG. 10(c) a step of injecting and incubating a specimen, and FIG. 10(d) a step of washing, and FIG. 10(e) a step of recovering a specimen. In FIGS. 10(a) to 10(e), reference numeral 31 indicates a group of thin wires (magnetic substance), 32 a non-magnetic support, 33 a reactor, 34 a valve, 35 a magnetic-labeled antibody, 36 a rare earth permanent magnet, 37 a yoke for generating gradient magnetic field, 38 a specimen, 39 washing solution, 40 a receptacle, and 41 a vibrator.

The reactor 33 is a glass vessel having heterogeneous cross-section with the lower side being narrower than the upper side and having a constricted shape in the central portion thereof. From the constricted portion to the lower portion of th reactor 33 a group of magnetic thin wires are hanged down. On the both side of the reactor 33 are detachable set a magnet 36 and a yoke 37 made of pure iron. The group of the magnetic thin wires are formed of nickel wire of a purity of 99.9% or higher and having an outer diameter of 0.15 mm shaped in the form of coil, and attached to a non-magnetic support rod 32 made of a glass rod, hanging in the reactor 33 between the reactors magnets 36, 36. The magnetic field formed by the magnet 36 was about 65 kG at a magnetic gap distance of 3 mm. The yoke 37 is used as a pair with the magnet 36, and the distance between a pair of yokes 37, 37 is constructed such that the distance therebetween increases according as they become remoter from the magnet 36, and therefore, there is generated in the vessel 33 a gradient magnetic field the higher the closer to the magnet 36.

The magnetic-labeled antibody 35 is superparamagnetic ultramicro-particles of magnetite having an average particle size of 5 nm, and the surface thereof is coated with dextran and an antibody which can react specifically with virus or cells to be detected is bound to the dextran via covalent bond.

Next, the method of preparing a specimen of the present invention will be described.

In the step of injecting the magnetic-labeled antibody shown in FIG. 10(a), a buffer solution containing $1 \times 10^{-8}$ g of the magnetic-labeled antibody 35 is injected to the reactor 33 with micro-syringe, the magnetic-labeled antibody 35 is dispersed uniformly in the buffer solution under the conditions under which the magnet 36 is not set.

Then, in the step of holding the magnetic-labeled antibody shown in FIG. 10(b), the magnet 36 and the yoke 37 are set in the condition that they are close to the magnetic thin wires 31, the magnetic-labeled antibody 35 in the reactor 33 guided to the magnetic thin wires 31 by gradient magnetic field and magnetically adsorbed by the magnetized magnetic thin wires 31. When the yoke 37 is absent, it take half a day or more to completely catch the magnetic-labeled antibody 35 floating remote from the magnet 36 on the magnetic thin wires 31. However, in this example in which the yoke 37 is set, they can be caught in about 5 minutes. The above-described injection and holding steps were divided for ease of explanation but in practice simultaneous use is more efficient. That is, the buffer solution containing the magnetic-labeled antibody 35 can be injected into the reactor 33 under the conditions where the magnet 36 is set.

FIG. 10 (c) shows a step of injection and incubation of a specimen, in which a valve 34 for the reactor 33 is opened to some extent and the specimen 38 is injected to the reactor 33 with a micro-syringe, such that the specimen 38 drops slowly in a small amount at a time. In this step, the specimen 38 passes around the magnetic thin wires 31 on which the magnetic-labeled antibody 35 is held, and upon passing there the specimen reacts with the magnetic-labeled antibody by an antigen-antibody reaction. In order to promote the antigen-antibody reaction, the reactor 33 is preferably heated to a temperature of 35° to 37° C. The flow rate is controlled by the valve 34, for example at a rate of 1 to 10 ml/hour.

Furthermore, the magnetic thin wires 31 may be oscillated or vibrated up and down by a vibrator 41 at a frequency of 0.5 to 10 Hz, at a width of about 0.5 to 3 mm. to give mild oscillation to accelerate the antigen-antibody reaction.

In the washing step shown in FIG. 10(d), the valve 34 is open and washing solution composed of TWEEN buffer solution is poured in the reactor 33 to wash out other substances than those adsorbed magnetically on the magnetic thin wires 31 into a receptor or dish 40.

In the recovering step shown in FIG. 10(e), the valve 24 is closed to fill the reactor with the washing solution to such an extent that the magnetic thin wires 31 is dipped entirely in the washing solution 39, and after removing the magnets 36, 36, the magnetic support rod 32 is vibrated by means of the vibrator 41 to completely release the complex between the magnetic-labeled antibody 35 an the specimen from the magnetic thin wires 31, then the valve is open to recover the specimen in the test vessel.

To the thus-prepared specimen can be applied a laser magnetic immunoassay method and an apparatus using superparamagnetic-labeled body. The method uses a gradient magnetic field generating device including an electromagnet, a pole piece placed opposite the electromagnet, in which the test vessel is inserted in the gradient magnet field generating device and outgoing light such as scattered light and the like from the specimen concentrated on the water surface just below the pole piece is detected. The method does not require B/F separation. That is, the magnetic-labeled body obtained as the result of an antigen-antibody reaction between the specimen and the magnetic-labeled body has a volume larger than that of unreacted magnetic-labeled body, and therefore, Brownian movement becomes inert. Therefore, the magnetic-labeled body bound to the specimen can be guided and concentrated in the gradient magnetic field easier than the unreacted magnetic-labeled body. The above-described method utilizes this feature. For example, the reacted and unreacted can be distinguished therebetween from a chronological change in the pattern of scattered light.

When the method for preparing a specimen described above is applied to a model experiment in which influenza virus in gargling water from a patient is detected, virus present in an aqueous solution in a population of several hundreds individuals per 10 ml can be detected in about 3 hours counted from the preparation of the specimen to measurement. The conventional method using eggs for cultivating influenza virus in gargling water from a subject until blood coagulation reaction becomes visible with one's eyes took several weeks before results were obtained.

Example 8

Figure 11:
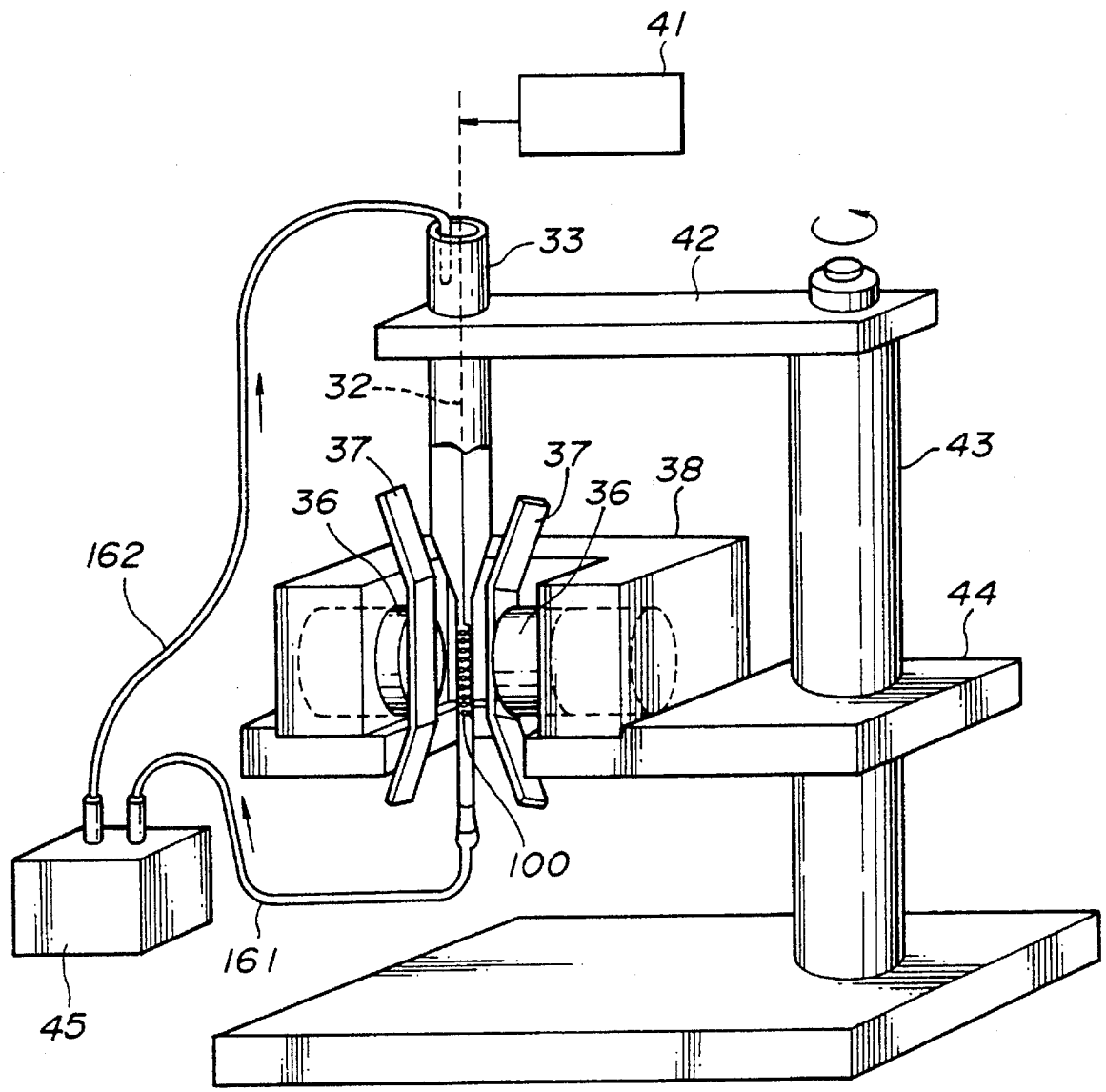
FIG. 11 is a schematic perspective view of a device for preparing a specimen according to a still another embodiment of the present invention.

FIG. 11 illustrates an example of the device for preparing a specimen according to the present invention. On an end surface of a rare earth magnet 36 which is cylindrical having a diameter of 20 m, a length of 20 mm, is magnetically adsorbed yoke 37 10 mm wide and 2 mm thick made of pure iron bent as shown in FIG. 10, and two magnets and yokes are arranged in an opposite relation and we attached to a magnet pair holder 38 with a open box (cross-section) form with magnetic gap distance of 2.5 mm. to constitute a gradient magnetic field generating device. In this case, the magnetic field of the magnetic gap portion is 7 kG.

The portion with a smaller cross-section inside the reactor 33 comprised of a Pasteur pippette is provided a coil (magnetic member) 100 made of nickel wire of 99.9% purity and having a wire diameter of 0.2 mm. In this example, the coil 100 corresponds to the magnetic thin wires 31 in the preceding example, and having a size of 1 mm in outer diameter and about 10 mm in length. The coil 100 is supported vertically by a plastic rod of 15 mm in diameter.

The reactor 33 is supported by a rotary stage 42' and is rotatable in a horizontal plane around the support 43 pole, and the gradient magnetic field generator is mounted on a stage 44 so that the coil 100 can be placed in the center of the gradient magnetic field generator.

As in this example, when the magnetic gap is reduced using the reactor having a heterogeneous cross-section, sufficient magnetic field can be generated with the permanent magnet 36 and the gradient magnetic field generator can be reduced in size advantageously. The reactor 33 is communicated with the pump 45 for circulation via pipings 161 and 162 made of silicone tube of 2 mm in outer diameter and 1 mm in inner diameter. The pump 45 is preferably a pump whose flow rate can be varied in the range of 1 to 100 ml/hour, for example, a perista pump (Pharmacia, P-1) is suitable. The vibrator 41 may be of any construction as far as it can give the non-magnetic support rod 2 minute oscillation up and down or from left to right. Ultrasonic oscillator, mechanical eccentric cam, etc. can be used. In this example, a construction including a piezoelectric element and a non-magnetic rod 32 attached thereto is used.

The operation of the device in this example is similar to that in Example 7 and will also be referred to in Example 9 below and detailed explanation is omitted here.

Example 9

In this example, the device in Example 8 was used to and the present invention was practiced using inactivated influenza virus which is highly safe for carrying experiments.

As pretreatment, non-magnetic particles of acrylic polymer of 1 μm in particle size, activated so as to adhere non-specifically to virus were used and after a specimen was caught up on the non-magnetic particles, with incubating at 35° C. for 2.5 hours, the surface of the non-magnetic particles where no virus is bound was coated with BSA to inactivate the non-magnetic particles. The object of catching virus with the non-magnetic particles beforehand was to remove unreacted magnetic-labeled antibody as described hereinbelow. The non-magnetic particles on which virus was caught was dispersed in 2 ml of HEPES buffer, and to this suspension was added a solution having added therein $1 \times 10^{-8}$ g of magnetic-labeled antibody having as a core magnetite micro-particles having an average particle size of 30 nm, and the mixture was injected in the reactor 33 in the device shown in FIG. 11 with circulating the mixture by the pump 45 and the specimen was magnetically adsorbed on the coil 100 by means of the magnet 36.

In Example, 7, an example is explained in which the magnetic-labeled antibody was first added to the reactor 33. However, in a method in which the specimen is circulated as in this example, the order of addition of the magnetic-labeled antibody and the specimen is not important since while the magnetic-labeled antibody and the specimen are circulating, the specimen after the antigen-antibody reaction is magnetically adsorbed on the coil 100 together with the magnetic-labeled antibody.

After incubating the specimen by circulating it at 35° C. for 2.5 hours, HEPES buffer was removed to a level of 0.5 ml, and the reactor 33 was rotated together with the rotary stage 42 to remove the reactor from the magnetic 36. Thereafter, the non-magnetic support rod 32 was vibrated to release the specimen from the coil 100, and then the specimen was recovered in the test vessel.

The recovered HEPES buffer solution contained unreacted magnetic-labeled antibody as well as the specimen bound to the magnetic-labeled antibody. Hence, for B/F separation, i.e., in order to separate unreacted magnetic-labeled antibody from magnetic-labeled specimen, the reaction mixture was centrifuged at 1,500 rpm for 5 minutes, and precipitate obtained was picked up in the test vessel, followed by measurement by the laser magnetic immunoassay using interference method described in WO/88/02118 to detect virus.

As the result, virus in gargling water in a concentration in the order of 10 individuals was successfully detected.

Although in the preceding examples, the magnetic member 31 in the form of coil was used, the shape of the magnetic member is not limited to coils but any shape may be selected as far as it can increase the probability of encounter between the magnetic-labeled antibody and the specimen. Therefore, the magnetic member may be a dendride, ladder form or torus form.

Example 10

Figure 12:
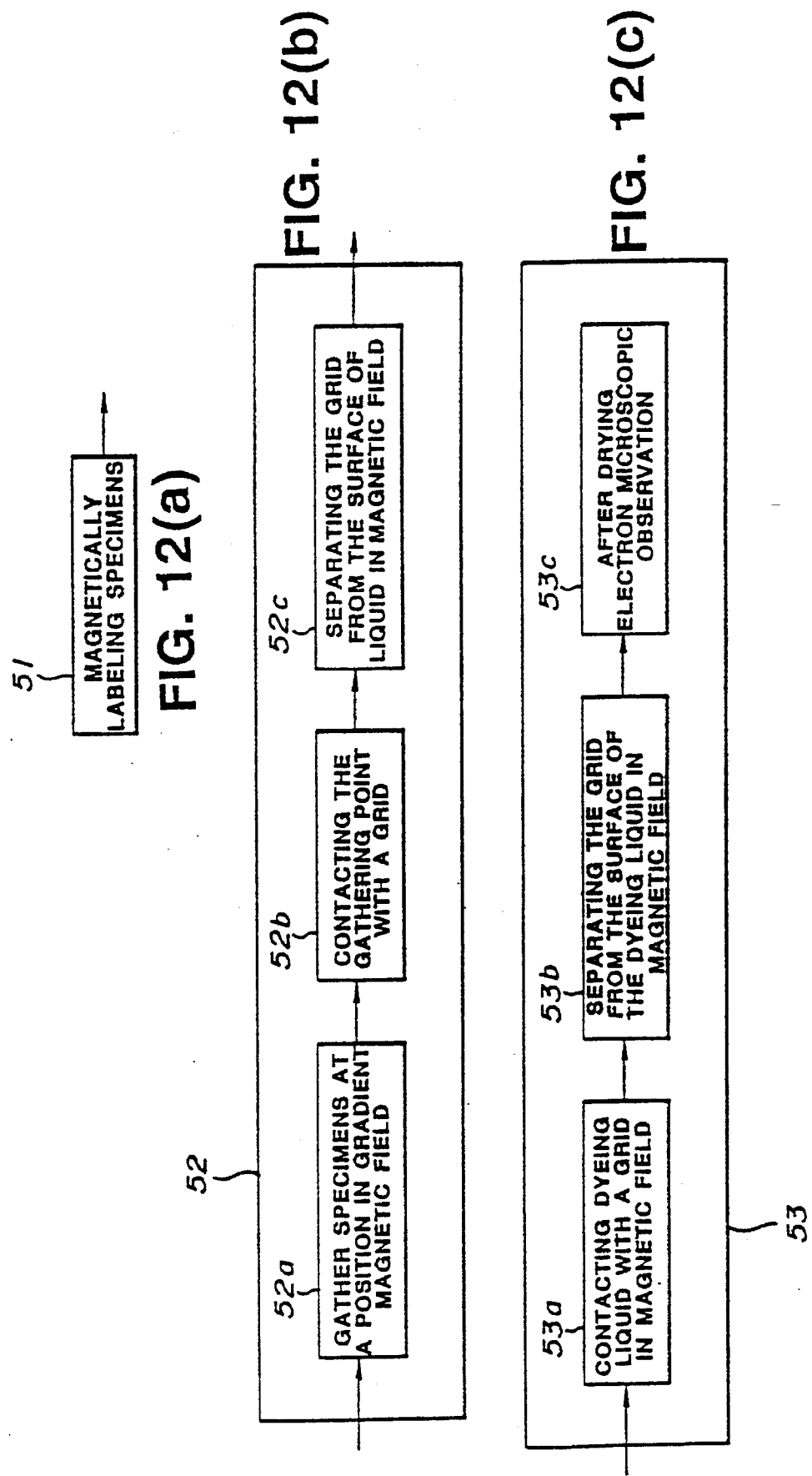
FIGS. 12(a), 12(b) and 12(c) are diagrammatic flow diagrams illustrating a method for preparing a specimen to be examined with an electron microscope according to yet another embodiment of the present invention.

FIG. 12 illustrates a flow chart of the method of preparing a specimen according an example of the present invention. This method comprises a first step 51 in which a specimen is magnetically labeled, a second step 52 in which the specimen is guided and fixed to a grid in gradient magnetic field and a third step 53 of performing negative staining in gradient magnetic field. The specimen used in this example was type A influenza virus (A/Ishikawa/7/82(H3N2)). It was confirmed that the specimen contained virus in a population of 1,000,000 individuals/ml as the result of blood coagulation reaction and blood cell calculating plate.

Referring to the first step of this example, antibody used for magnetic labeling is IgG obtained by purifying rabbit hyperimmune antiserum to virus. This was bound by covalent bonding to a dextran-coated magnetic micro-particle of magnetite having an average particle size of 10 nm to obtain magnetic-labeled antibody. The labeling of the specimen was performed by incubating I ml of the specimen and 10 μm of the magnetic-labeled antibody at 35° C. for 2.5 hours.

Now reference is made to the second step 52 of this example which is divided into three sub steps 52a, 52b and 52c. The first sub step 52a is a step in which the specimen is locally concentrated in gradient magnetic field, and the second sub step 52b is a step in which a grid is connected with the position of local concentration, and the third sub steps 52c is a step in which a grid is removed from the water surface with applying magnetic field.

Figure 13:
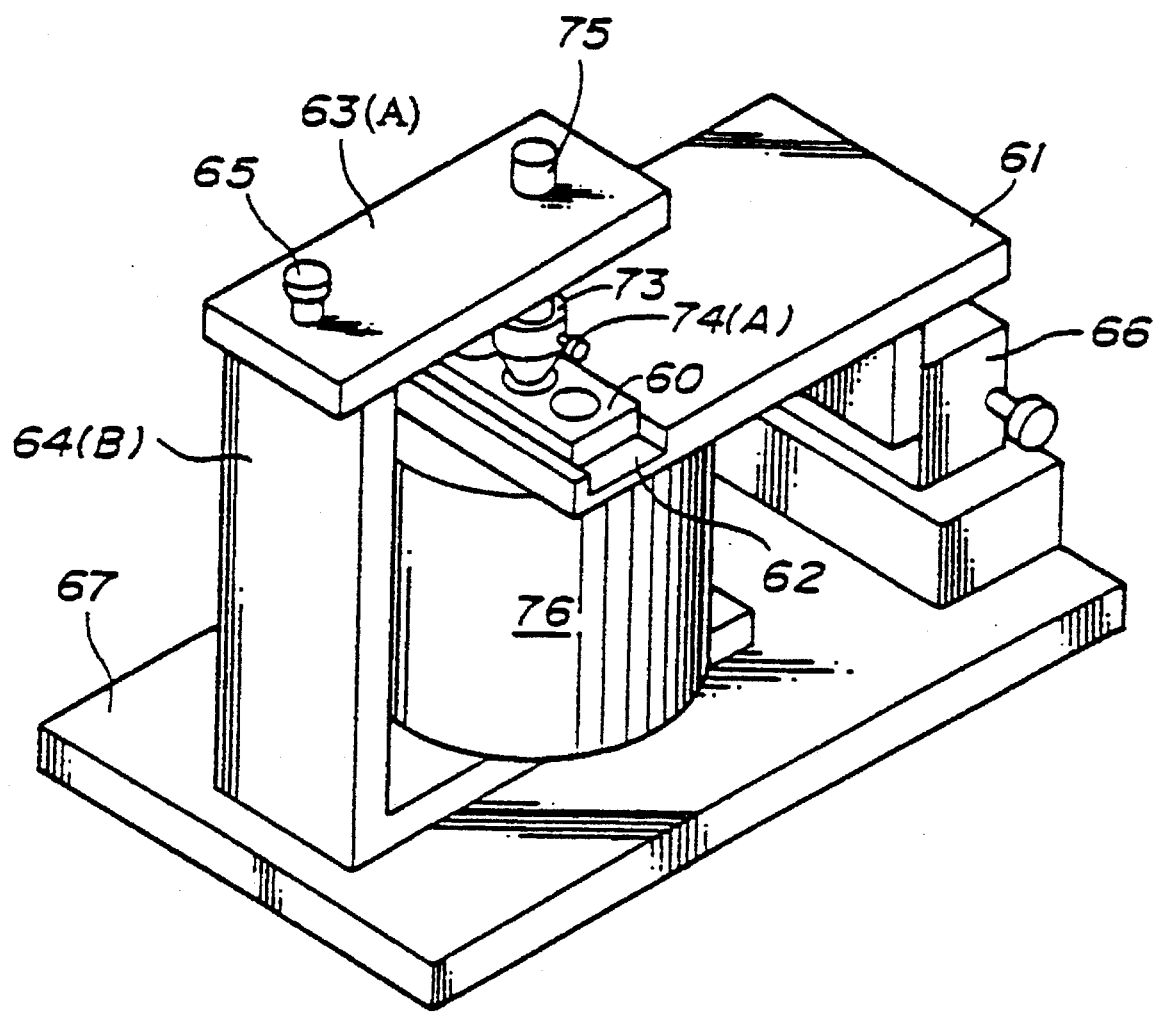
FIG. 13 is a schematic perspective view showing the construction of a device for preparing a specimen to be examined with an electron microscope according to an embodiment of the present invention.

FIG. 13 is a schematic view illustrating the construction of the device for preparing a specimen for use in electron microscopic observation. In FIG. 13, reference numeral 76 indicates an electromagnet, 60 a vessel, 61 a vessel support sage, and 62 a guide face for guiding the vessel. The vessel 60 is set on the guide face 62, and is attached to a height control sage 66. The vessel support stage 61 can be controlled to a desired height by means of the height control stage 66.

In FIG. 13, reference numeral 63 indicates indicates a yoke (A) for holding the pole piece 75, and 64 a yoke (B). The yoke (A) 63 is linked to the yoke (B) 64 through a yoke clamp screw 65 for clamping a yoke and can fix the yoke 63 in any direction as shown in FIG. 13. The magnetic flux outgoing the electromagnet 76 is converged by the pole piece (B) 75 after passing the vessel 60 and going back to the electromagnet 76 through the yoke (A) 63 and the yoke 64 (B), thus forming a magnetic circuit. When the distance between the electromagnet 76 and the pole piece (B) 62 was 11 mm, the magnetic field generated upon application of current of 1 A to the electromagnet 76 at the position 0.5 mm just below the pole piece (B) 62 was 8 kG.

Figure 14:
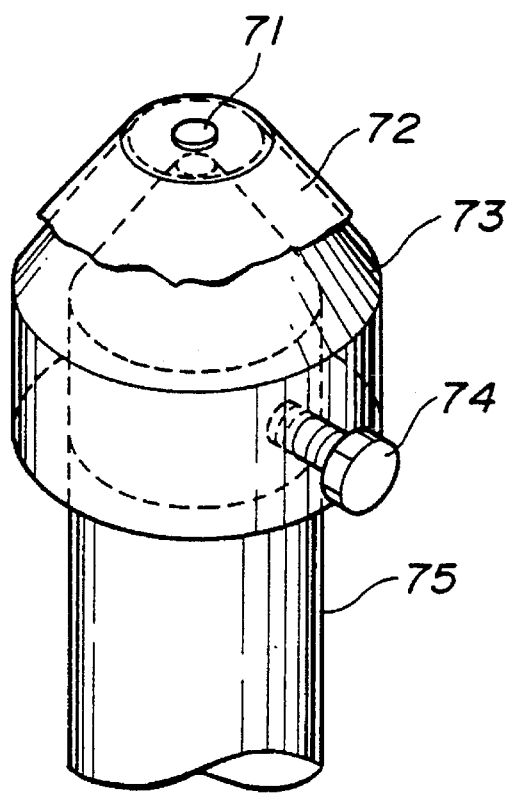
FIG. 14 is a schematic partial perspective view of a portion for mounting a grid for use in electron microscopic observation in a device for preparing a specimen to be examined with an electron microscope.

As shown in FIG. 13, on the tip of the pole piece 75 is attached a grid mount stage 73. The grid mount stage 73 is made of a plastic and is clamped to the pole piece 75 with a stop screw 74. On the grid mount stage 73 is bonded a copper grid 71 (see FIG. 14) having a diameter of about 3 mm with an adhesive film (parefilm) 72 (See FIG. 14). The distance between the tip of the pole piece 75 and the grid 71 is preferably as close as possible for generating strong magnetic field and the distance is set up 1 mm in this example.

After bonding the grid 71 on the grid mount stage 73, and after fitting the grid mount stage 73 to the pole piece 75, the second step 52 is initiated. The first sub step 52a was performed as follows. At first, a washing solution composed of PBS-Tween was charged beforehand in the reactor 60 in an amount of 1 ml, and 25 μl of a solution containing the magnetic-labeled specimen obtained in the first step 51 above was injected thereto to obtain a specimen suspension. Then, the electromagnet 76 was energized to generate gradient magnetic field, and the magnetic-labeled specimen was locally concentrated on the liquid surface just below the pole piece 75. In the second sub step 52b, the height control stage 66 was operated to upwardly move the vessel 60 to bring the grid 7 in contact with liquid surface. This operation caused the magnetic-labeled specimen to be magnetically adsorbed onto the rear surface of the pole piece 75, and guided and fixed on the grid 71 naturally. Then, in the third sub step 52c, while the electromagnet 76 is energized, the grid mount stage 73 was removed from the liquid surface by lowering the height control stage 66. With the above procedures, the magnetically labelled specimen was recovered on the grid 71.

The third step 53 comprises the following three sub steps 53a, 53b and 53c. Upon initiating the third step 53, at first a staining liquid composed of 1% phosphotungstic acid was charged in another well in the vessel 60, and the staining liquid was moved to a position just below the grid mount stage 73 along the vessel guide face 62. Then, in the sub step 53a, the vessel 60 was moved upward by the operation of the height control stage 66 while keeping energizing the electromagnet 76 to bring the grid in contact with the liquid surface. After a predetermined period of time, in this example after 30 seconds, the height control stage 66 was lowered to remove the height control stage 66 to thereby remove the grid mount stage 73 from the liquid surface, thus effecting the second sub step 53b. Thereafter, in the third sub step 53c, excessive staining liquor was removed with filter paper followed by natural drying, (air drying), thus completing the staining of the specimen.

The detection limit was examined with applying the above-described method for preparing a specimen to influenza virus. By serially diluting at a dilution ratio of 1/10 the original with PBS solution, the detection limit with electron microscopic observation of virus was examined. As the result, screening of virus was successful with case under electron microscopy with the range of vision at a magnification ratio of 50,000 times even in a virus concentration in the order of 1,000 individuals/ml.

For comparison, electron microscopic observation was performed according to the conventional method in which no magnetic labeling was performed, the presence of virus was not confirmed even with non-diluted specimen.

A/though in the above description, the specimen vessel 60 was moved up and down, similar results could be obtained when the pole piece 75 attached to the grid mount stage 73 was moved up and down.

Example 11

Prior to the first step for magnetically labeling specimens as explained in Example 10, a step for gathering virus was performed. Specifically, IgG antibody of 20 µl used in Example 10 was added to specimen of 1 ml used in Example 10. The resulting mixture was subjected to incubation in two steps including a first step which was performed at a temperature of 35° C. for second incubation period of 2.4 hours, and a second step which is performed at a temperature of 4° C. for a second incubation period of one night to thereby gather virus particles to each other. After this step, the process for preparing specimen was performed by the same procedures in Example 10. In further steps, the specimens were subjected to ultracentrifuging. The ultracentrifuging was performed at a revolution rate of 3,000 rpm for 30 minutes to precipitate an immunocomplex including virus and an IgG antibody. The resulting precipitates were redispersed into PBS solution. The difference between Example 10 and Example 11 is only that particles obtained by binding ultramicro-particles coated by dextrans with Protein A were used as the antibody labelled with the pole piece. Accordingly, Protein A connects specifically to an IgG antibody, and virus particles to be gathered by means of IgG antibody are magnetically labelled with magnetic micro-particles. Accordingly, pretreatment for gathering virus each other is previously performed prior to observation by means of electron microscope, so that the electron microscopic observation is easily carried out. When the concentration of virus is about 100 individual/ml, the observation can be easily performed. The process for performing easily the electron microscopic observation by gathering previously specimens is known as a method for preparing specimens for the electron microscopic observation. However, the conventional method does not include a step for labeling magnetically specimens according to the process of the present invention. The process of the present invention has a detection sensitivity higher by five digits than the conventional method.

It is noted that although the present invention is applied to the observation of virus, various kinds of cells such as cancer cells, lymphocyte, and the like may be used as the objects of the observation described above.

In the process of the present invention, the following processes can be used. For example, a process for staining in negative specimens disposed on a grid and then observing the stained specimens, a process for embedding specimens in resins, cutting the resins to obtain a slice, and observing the slice, and the like can be applied to the present invention. More specifically, according to the conventional processes when the slice of the specimens is formed, the specimens must be subjected to fixation dehydration, and burying while centrifuging the specimens many times. According to the process for preparing specimens of the present invention, the step of centrifuging specimens must not be performed. Specifically, in the present invention, the specimens can be introduced and kept at a predetermined position in a gradient magnetic field. Accordingly, the fixation of of the specimens and the dehydration by using alcohols can be easily carried out. Also, when burying specimens, they can be cut with ease by using a microtome because they are gathered to a predetermined position.

What is claimed is:

1. A device for collecting a specimen, comprising:

(a) a vessel, for containing a solution having an immunocomplex, wherein said immunocomplex is a result of an antigen-antibody reaction between a specimen and a magnetic-labeled antibody comprising a magnetic micro-particle and an antibody fixed to the magnetic micro-particle;

(b) an external magnetic field generating device, for generating a gradient magnetic field and applying said gradient magnetic field to the solution in the test vessel to cause local concentration of the immunocomplex to a predetermined position, wherein said magnetic field generating device includes an electromagnet, a pole piece, and a yoke, such that the magnetic flux from the electromagnet passes through the test vessel, is gathered by the pole piece, and returns to the electromagnet via the yoke, thereby forming a magnetic circuit;

(c) a magnetic member, movably positioned in a lengthwise hole through the center of the pole piece, for collecting the immunocomplex at the position of local concentration; and (d) a moving mechanism, for effecting relative movement between the magnetic member and the test vessel.

2. The device of claim 1, wherein the magnetic member is a magnetized nickel wire.

3. The device of claim 2, wherein the mechanism for effecting relative movement between the magnetic member and the test vessel is a winch.

4. A device for preparing a specimen, comprising:
   (a) a vessel for containing a solution having an immunocomplex, wherein said immunocomplex is a result of an antigen-antibody reaction between a specimen and a magnetic-labeled antibody comprising a magnetic micro-particle and an antibody fixed to the magnetic micro-particle;
   (b) an external magnetic field generating device, for generating a gradient magnetic field and applying said gradient magnetic field to the solution in the test vessel to cause local concentration of the immunocomplex to a predetermined position, wherein said magnetic field generating device includes an electromagnet having an iron core, a movable first pole piece, and a yoke, such that the magnetic flux from the electromagnet passes through the test vessel, is gathered by the first pole piece, and returns to the electromagnet via the yoke, thereby forming a magnetic circuit;
   (c) a recovery mechanism for recovering the immunocomplex, wherein said recovery mechanism comprises a capillary tube removably positioned in a lengthwise hole through the center of the first pole piece;
   (d) a guide mechanism, for guiding the immunocomplex onto the surface of a grid for use in electron microscopic observation and for holding the grid while fixing the immunocomplex on the grid, wherein said guide mechanism comprises a second pole piece for mounting onto the iron core of the electromagnet and a grid stage for mounting onto the second pole piece.

5. A device for preparing a specimen, comprising:
   (a) a reaction vessel comprising a hollow tube, for containing a magnetic-labeled antibody comprising a magnetic micro-particle and an antibody, which binds to the specimen, fixed to the magnetic micro-particle;
   (b) a magnetic member comprising a coiled magnetic wire provided inside the reaction vessel for collection of the magnetic-labeled antibody, wherein said coiled magnetic wire is attached to and supported by a non-magnetic rod;
   (c) a gradient magnetic field generating mechanism, for generating a gradient magnetic field, comprising a pair of cylindrical magnets and a yoke disposed at an end of each of said magnets, said magnets disposed outside of and adjacent to said reaction vessel; and
   (d) a vibrator, for vibration of said non-magnetic rod attached to said coiled magnetic wire, to provide circulation of the specimen through the gradient magnetic field and release of the magnetic-labeled antibody subsequent to removal of the magnets.

6. The device of claim 5, wherein the magnetic member is a magnetic nickel wire.

7. A device for preparing a magnetically-labeled specimen, comprising:
   (a) a gradient magnetic field generating means, for generating a gradient magnetic field to effect local concentration of the magnetically-labeled specimen at a predetermined position;
   (b) a grid holder, for holding a grid used in electron microscopic observation, said grid holder disposed above said gradient magnetic field generating means; and
   (c) a guide means for guiding the grid holder to said predetermined position.

* * * * *